(12) United States Patent
Cinader, Jr.

(10) Patent No.: US 9,539,065 B2
(45) Date of Patent: Jan. 10, 2017

(54) ASSEMBLIES, METHODS, AND KITS INCLUDING A COMPRESSIBLE MATERIAL

(75) Inventor: David K. Cinader, Jr., Walnut, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 607 days.

(21) Appl. No.: 12/428,989

(22) Filed: Apr. 23, 2009

(65) Prior Publication Data

US 2009/0233252 A1    Sep. 17, 2009

Related U.S. Application Data

(63) Continuation-in-part of application No. 11/551,823, filed on Oct. 23, 2006, now abandoned.

(51) Int. Cl.
*A61C 3/00* (2006.01)
*A61C 7/14* (2006.01)

(52) U.S. Cl.
CPC .......... *A61C 7/14* (2013.01); *A61C 7/146* (2013.01); *A61C 2202/00* (2013.01); *A61C 2202/01* (2013.01)

(58) Field of Classification Search
CPC .......... A61C 7/12; A61C 7/14; A61C 7/28; A61C 7/18; A61C 7/16; A61C 2202/01
USPC .......................................... 433/8–17, 18–24
See application file for complete search history.

(56) References Cited

U.S. PATENT DOCUMENTS

| | | | |
|---|---|---|---|
| 3,018,262 A | 1/1962 | Schroeder | |
| 4,148,988 A * | 4/1979 | Masuhara et al. | 526/318 |
| 4,172,323 A * | 10/1979 | Orlowski | 433/180 |
| 4,180,911 A * | 1/1980 | Bullock | 433/9 |
| 4,259,075 A | 3/1981 | Yamauchi et al. | |
| 4,298,738 A | 11/1981 | Lechtken et al. | |
| 4,303,730 A | 12/1981 | Torobin | |
| 4,324,744 A | 4/1982 | Lechtken et al. | |
| 4,336,338 A | 6/1982 | Downs et al. | |
| 4,356,296 A | 10/1982 | Griffith et al. | |
| 4,380,432 A * | 4/1983 | Orlowski et al. | 433/9 |
| 4,385,109 A | 5/1983 | Lechtken et al. | |
| 4,499,251 A | 2/1985 | Omura et al. | |
| 4,503,169 A | 3/1985 | Randklev | |
| 4,537,940 A | 8/1985 | Omura et al. | |

(Continued)

FOREIGN PATENT DOCUMENTS

| | | |
|---|---|---|
| EP | 0 173 567 A2 | 3/1986 |
| EP | 0 173 567 A3 | 3/1986 |

(Continued)

OTHER PUBLICATIONS

Lee and Neville, Handbook of Epoxy Resins, McGraw-Hill Book Co., New York, 1967.

(Continued)

*Primary Examiner* — Yogesh Patel

(57) ABSTRACT

The present invention provides assemblies, kits, and methods including a compressible material. Optionally, a hardenable dental composition (e.g., an adhesive or primer) is in contact with the compressible material for bonding a dental article (e.g., an orthodontic appliance) to a tooth structure. Removal of excess hardenable and/or hardened dental composition, if desired, can be facilitated for embodiments in which the hardenable dental composition is an unfilled or a lightly filled composition.

56 Claims, 3 Drawing Sheets

(56) References Cited

U.S. PATENT DOCUMENTS

| | | | |
|---|---|---|---|
| 4,539,382 A | 9/1985 | Omura et al. | |
| 4,605,402 A | 8/1986 | Iskra | |
| 4,642,126 A | 2/1987 | Zador et al. | |
| 4,648,843 A | 3/1987 | Mitra | |
| 4,652,274 A | 3/1987 | Boettcher et al. | |
| 4,665,217 A | 5/1987 | Reiners et al. | |
| 4,677,139 A * | 6/1987 | Feinmann et al. | 128/888 |
| 4,695,251 A | 9/1987 | Randklev | |
| 4,710,523 A | 12/1987 | Lechtken et al. | |
| 4,737,593 A | 4/1988 | Ellrich et al. | |
| 4,752,338 A | 6/1988 | Reiners et al. | |
| 4,865,596 A | 9/1989 | Weisman et al. | |
| 4,872,936 A | 10/1989 | Engelbrecht | |
| 4,954,414 A * | 9/1990 | Adair et al. | 430/138 |
| 4,978,007 A | 12/1990 | Jacobs et al. | |
| 5,008,304 A | 4/1991 | Kmentt | |
| 5,015,180 A * | 5/1991 | Randklev | 433/9 |
| 5,026,902 A | 6/1991 | Fock et al. | |
| 5,037,861 A | 8/1991 | Crivello et al. | |
| 5,045,569 A | 9/1991 | Delgado | |
| 5,063,257 A | 11/1991 | Akahane et al. | |
| 5,076,844 A | 12/1991 | Fock et al. | |
| 5,098,288 A | 3/1992 | Kesling | |
| 5,110,290 A * | 5/1992 | Wong | 433/9 |
| 5,130,347 A | 7/1992 | Mitra | |
| 5,154,762 A | 10/1992 | Mitra et al. | |
| 5,172,809 A | 12/1992 | Jacobs et al. | |
| 5,176,951 A | 1/1993 | Rudo | |
| 5,219,283 A | 6/1993 | Farzin-Nia et al. | |
| 5,227,413 A | 7/1993 | Mitra | |
| 5,256,064 A | 10/1993 | Riihimaki et al. | |
| 5,263,859 A | 11/1993 | Kesling | |
| 5,328,363 A | 7/1994 | Chester et al. | |
| 5,367,002 A | 11/1994 | Huang et al. | |
| 5,501,727 A | 3/1996 | Wang et al. | |
| 5,520,725 A | 5/1996 | Kato et al. | |
| 5,530,038 A | 6/1996 | Yamamoto et al. | |
| 5,545,676 A | 8/1996 | Palazzotto et al. | |
| 5,614,570 A | 3/1997 | Hansen et al. | |
| 5,722,826 A * | 3/1998 | Tuneberg et al. | 433/9 |
| 5,746,594 A * | 5/1998 | Jordan et al. | 433/9 |
| 5,770,636 A | 6/1998 | Wernsing et al. | |
| 5,810,584 A | 9/1998 | Wong | |
| 5,817,704 A | 10/1998 | Shiveley et al. | |
| 5,827,058 A * | 10/1998 | Kelly | A61C 7/12 206/368 |
| 5,829,973 A * | 11/1998 | Andreiko et al. | 433/9 |
| 5,846,640 A | 12/1998 | Vallittu | |
| 5,856,373 A | 1/1999 | Kaisaki et al. | |
| 5,859,089 A | 1/1999 | Qian | |
| 5,861,214 A | 1/1999 | Kitano et al. | |
| 5,871,360 A | 2/1999 | Kato | |
| 5,890,892 A * | 4/1999 | Lemchen | 433/9 |
| 5,925,715 A | 7/1999 | Mitra | |
| 5,938,435 A * | 8/1999 | Raspino, Jr. | 433/2 |
| 5,962,550 A | 10/1999 | Akahane et al. | |
| 5,965,632 A | 10/1999 | Orlowski et al. | |
| 5,971,754 A | 10/1999 | Sondhi et al. | |
| 6,027,795 A | 2/2000 | Kabra et al. | |
| 6,030,606 A | 2/2000 | Holmes | |
| 6,050,815 A * | 4/2000 | Adam et al. | 433/9 |
| 6,071,983 A | 6/2000 | Yamamoto et al. | |
| 6,084,004 A | 7/2000 | Weinmann et al. | |
| 6,089,861 A | 7/2000 | Kelly et al. | |
| 6,183,249 B1 * | 2/2001 | Brennan et al. | 433/9 |
| 6,187,833 B1 | 2/2001 | Oxman et al. | |
| 6,187,836 B1 | 2/2001 | Oxman et al. | |
| 6,245,828 B1 | 6/2001 | Weinmann et al. | |
| 6,251,963 B1 | 6/2001 | Köhler et al. | |
| 6,331,080 B1 | 12/2001 | Cole et al. | |
| 6,387,981 B1 | 5/2002 | Zhang et al. | |
| 6,444,725 B1 | 9/2002 | Trom et al. | |
| 6,458,868 B1 | 10/2002 | Okada et al. | |
| 6,482,003 B2 * | 11/2002 | Dixon et al. | 433/9 |
| 6,528,555 B1 | 3/2003 | Nikutowski et al. | |
| 6,572,693 B1 | 6/2003 | Wu et al. | |
| 6,645,618 B2 | 11/2003 | Hobbs et al. | |
| 6,669,927 B2 | 12/2003 | Trom et al. | |
| 6,670,436 B2 | 12/2003 | Burgath et al. | |
| 6,750,261 B1 | 6/2004 | Clear et al. | |
| 6,765,036 B2 | 7/2004 | Dede et al. | |
| 6,765,038 B2 | 7/2004 | Mitra | |
| 6,960,079 B2 | 11/2005 | Brennan et al. | |
| 7,090,721 B2 | 8/2006 | Craig et al. | |
| 7,090,722 B2 | 8/2006 | Budd et al. | |
| 2003/0003421 A1 | 1/2003 | Bestenheider et al. | |
| 2003/0035899 A1 | 2/2003 | Klettke et al. | |
| 2003/0114553 A1* | 6/2003 | Karim et al. | 523/115 |
| 2003/0166740 A1 | 9/2003 | Mitra et al. | |
| 2003/0195273 A1 | 10/2003 | Mitra et al. | |
| 2003/0196914 A1 | 10/2003 | Tzou et al. | |
| 2003/0198913 A1 | 10/2003 | Cinader, Jr. et al. | |
| 2003/0198914 A1* | 10/2003 | Brennan et al. | 433/9 |
| 2004/0151691 A1 | 8/2004 | Oxman et al. | |
| 2004/0157185 A1* | 8/2004 | Andreiko | 433/9 |
| 2004/0206932 A1 | 10/2004 | Abuelyaman | |
| 2004/0219471 A1* | 11/2004 | Cleary et al. | 433/3 |
| 2005/0074716 A1 | 4/2005 | Cleary et al. | |
| 2005/0113477 A1 | 5/2005 | Oxman et al. | |
| 2005/0133384 A1* | 6/2005 | Cinader | A61C 7/16 206/63.5 |
| 2005/0136370 A1* | 6/2005 | Brennan et al. | 433/9 |
| 2005/0252413 A1 | 11/2005 | Kangas et al. | |
| 2005/0256223 A1 | 11/2005 | Kolb et al. | |
| 2006/0208393 A1 | 9/2006 | Karmaker et al. | |
| 2006/0257821 A1 | 11/2006 | Cinader et al. | |
| 2008/0113310 A1* | 5/2008 | Andreiko | 433/9 |
| 2008/0145820 A1 | 6/2008 | Karmaker et al. | |
| 2008/0250974 A1 | 10/2008 | Jia | |
| 2009/0065961 A1 | 3/2009 | Teo et al. | |
| 2009/0233252 A1 | 9/2009 | Cinader et al. | |
| 2013/0280669 A1* | 10/2013 | Cinader | A61C 7/14 433/9 |

FOREIGN PATENT DOCUMENTS

| | | |
|---|---|---|
| EP | 0 373 384 A1 | 6/1990 |
| EP | 0 373 384 B1 | 10/1992 |
| EP | 0 712 622 A1 | 5/1996 |
| EP | 0 897 710 A2 | 2/1999 |
| EP | 0 897 710 A3 | 2/1999 |
| EP | 0 712 622 B1 | 9/1999 |
| EP | 1 051 961 A1 | 11/2000 |
| EP | 0 897 710 B1 | 11/2004 |
| EP | 1 051 961 B1 | 2/2006 |
| JP | 60005143 | 1/1985 |
| JP | 63170437 | 7/1988 |
| JP | 4227252 | 8/1992 |
| JP | 06-285086 | 10/1994 |
| JP | 2002-360606 | 12/2002 |
| JP | 2003-505187 | 2/2003 |
| JP | 2007-523666 | 8/2007 |
| RU | 2246916 | 2/2005 |
| WO | WO 92/13576 A1 | 8/1992 |
| WO | WO 00/38619 A2 | 7/2000 |
| WO | WO 00/38619 A3 | 7/2000 |
| WO | WO 00/42092 A1 | 7/2000 |
| WO | WO 01/07444 A1 | 2/2001 |
| WO | WO 01/30305 A1 | 5/2001 |
| WO | WO 01/30306 A1 | 5/2001 |
| WO | WO 01/30307 A1 | 5/2001 |
| WO | WO 01/51540 A2 | 7/2001 |
| WO | WO 01/51540 A3 | 7/2001 |
| WO | WO 01/92271 A1 | 12/2001 |
| WO | WO 03/063804 A1 | 8/2003 |
| WO | WO 03/088928 A1 | 10/2003 |
| WO | WO 2006/096558 A2 | 9/2006 |
| WO | WO 2008/000917 A1 | 1/2008 |

OTHER PUBLICATIONS

Mathis et al., "Properties of a New Glass Ionomer/Composite Resin Hybrid Restorative," Abstract No. 51, J. Dent. Res., 66:113 (1987).

(56) References Cited

OTHER PUBLICATIONS

Nacht et al., "The microsponge: a novel topical programmable delivery system," *Topical Drug Delivery Formulations*, D.W. Osborn and A. H. Amman (Eds.), Marel Dekker, New York, pp. 299-325 (1990).
Westerman et al., "Effect of ethylene vinyl acetate (EVA) closed cell foam on transmitted forces in mouthguard material," *British Journal of Sports Medicine*, 2002, 36:205-208.
Bonding of brackets using a caries-protective adhesive patch, Journal of Dentistry 36 (2008) 125-129, Schmidlin et al.
Akin-Nergiz N.; Fortschritte der Kieferothopadie 1995;56(1): 49-55.
Wiechmann, Lingual Orthodontics (Part 3): Intraloral Sandblasting and Indirect Bonding; Journal of Orofacial Orthopedics, © Urban & Vogel Munchen, 2000;61-280-91.
Newman et al., Adhesion promoters, their effect on the bond strength of metal brackets, American Journal of Orthodontics and Dentofacial Orthopedics, Sep. 1995, vol. 108, No. 3, pp. 237-241.
Mujagic, et al., Digital Design and Manufacturing of the Lingualcare Bracket System, © Jun. 2005 JCO, Inc., vol. XXXIX, No. 6, pp. 375-382.
Atsu et al., Effects of Silica Coating and Silane Surface Conditioning on the Bond Strength of Metal and Ceramic Brackets to Enamel, Angle Orthodontist, vol. 76, No. 5, 2006, pp. 857-862.
U.S. Appl. No. 60/600,658 (Luchterhandt et al.), filed Aug. 11, 2004.
Supplementary European Search Report for Application No. 07854149.7-2318 / 2076202—PCT/US2007081708 mailed May 11, 2011.

\* cited by examiner

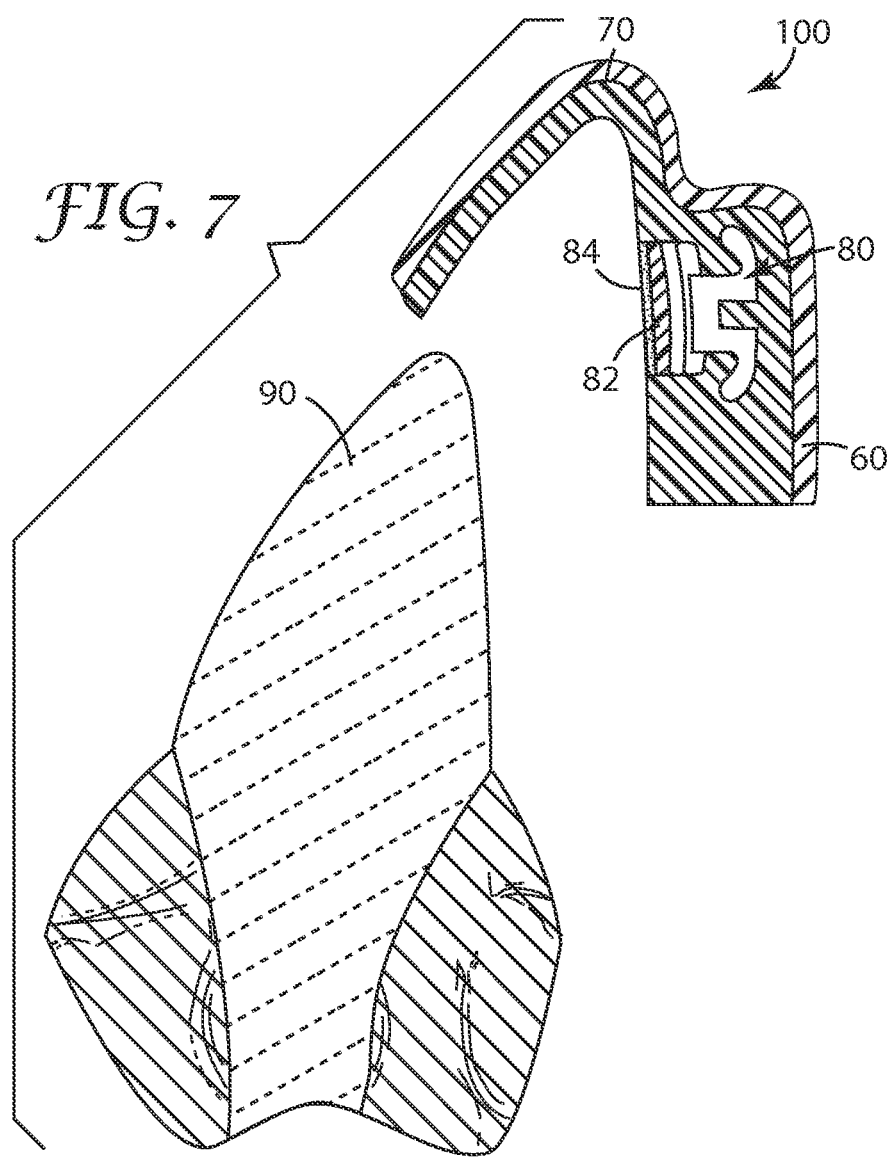

ASSEMBLIES, METHODS, AND KITS INCLUDING A COMPRESSIBLE MATERIAL

CROSS-REFERENCE TO RELATED APPLICATIONS

This application is a continuation-in-part of U.S. Ser. No. 11/551,823, filed Oct. 23, 2006 now abandoned, published as U.S. 2008/0096150.

BACKGROUND

Dental articles have been bonded to tooth structures for a wide variety of treatment regimens including, for example, orthodontic treatment. Orthodontic treatment involves movement of malpositioned teeth to orthodontically correct positions. Tiny orthodontic appliances known as brackets are connected to exterior surfaces of the patient's teeth, and an archwire is placed in a slot of each bracket. The archwire forms a track to guide movement of the teeth to desired positions for correct occlusion. End sections of the archwire are often received in appliances known as buccal tubes that are fixed to the patient's molar teeth. In recent years it has become common practice to use adhesives to bond orthodontic appliances to the surface of the tooth, using either direct or indirect methods. A variety of adhesives are available to the practitioner for bonding brackets to tooth surfaces, and many offer excellent bond strengths. High bond strengths are desirable for maintaining adhesion of the bracket to the tooth surface over the duration of the treatment process, which can typically be two years or more.

The use of a bonding method can typically require, among other steps, placing an amount of adhesive on a bracket or using a bracket having the adhesive precoated thereon, applying the bracket to the desired tooth structure, positioning the bracket to the desired location on the tooth, pressing the bracket to exude excess adhesive and achieve the clinically optimum location of the bracket, and removing excess adhesive. Conventional orthodontic adhesives are typically highly filled, which results in an adhesive with a white or tooth color. It is desirable that a sufficient but not an excess amount of adhesive is used to bond the bracket to the tooth structure. Excess adhesive on the tooth structure can eventually be a site for bacteria accumulation and/or staining from food or drink. Because orthodontic treatment can last from 18 to 36 months or more, bacteria accumulation can damage the tooth structure and may lead to discoloration of the adhesive, both of which are undesirable. Identifying and removing excess adhesive from tooth structure can be difficult if there is similarity in the adhesive color and the tooth color, i.e., due to a lack of a contrasting color in the adhesive. Color-changing adhesives that have an initial color that contrasts with the tooth structure have aided practitioners in the identification of excess adhesive. However, removal of the excess adhesive is typically still required.

New adhesives and methods are needed that offer satisfactory adhesion of a dental article to a tooth structure and simplify the removal of excess adhesive, if desired, upon application of the dental article to the tooth structure.

SUMMARY

In one aspect, the present invention provides an assembly including: a dental article (e.g., an orthodontic appliance) for bonding to tooth structure, the article having an outer surface; and a compressible material attached to the surface of the article. Preferably, the compressible material is mechanically bonded to the surface of the article, chemically bonded to the surface of the article, or a combination thereof. In certain embodiments, the compressible material includes a hardenable or partially hardened dental composition (e.g., a foamed dental composition). Optionally the assembly further includes a hardenable dental composition that can optionally be in contact with the compressible material. In certain embodiments, the hardenable dental composition is an unfilled or lightly filled composition.

In another aspect, the present invention provides a kit. In some embodiments, the kit includes one or more assemblies including: a dental article (e.g., an orthodontic appliance) for bonding to tooth structure, the article having an outer surface and a compressible material attached to the surface of the article. Optionally, the kit can further include instructions for using the assemblies as described herein. Optionally the kit can further include a hardenable dental composition, for example, that can be used in combination with the compressible material to bond the dental article to the tooth structure as described herein. In certain embodiments, the hardenable dental composition is an unfilled or lightly filled composition (e.g., a primer or a self-etching primer). In other certain embodiments, the kit further includes a self-etching primer, for example, that can be applied to the tooth structure prior to bonding the dental article to the tooth structure.

In still another aspect, the present invention provides a method for bonding a dental article to a tooth structure. In certain embodiments the method includes: providing a dental article (e.g., an orthodontic appliance) having an outer surface; providing a compressible material and a hardenable dental composition; contacting the compressible material and the hardenable dental composition with the tooth structure and the surface of the dental article; and hardening the dental composition. In certain embodiments, the dental article is provided as an assembly having the compressible material attached to the surface thereof. Optionally, the assembly further includes the hardenable dental composition in contact with the compressible material. In certain embodiments, the hardenable dental composition is an unfilled or lightly filled composition (e.g., a primer or a self-etching primer).

Assemblies, kits, and methods as described herein can be advantageously used for bonding dental articles (e.g., orthodontic appliances) to tooth structures. For example, conventional orthodontic adhesives utilize a high filler loading to enable the adhesive to fill the gap between the base of the orthodontic appliance and the tooth structure to provide adequate adhesive properties upon hardening. However, excess highly filled adhesive can be difficult or time-consuming for the practitioner to remove. Assemblies, kits, and methods as described herein optionally include the combination of (a) a compressible material that can fill the gap between the surface of a dental article (e.g., the base of an orthodontic appliance) and a tooth structure, and (b) a hardenable dental composition that can advantageously be unfilled or lightly filled. The combination of the compressible material and the unfilled or lightly filled hardenable dental composition can provide adequate handling properties for application and adequate adhesive properties upon hardening, while allowing for simplified removal, if desired, of excess dental composition by the practitioner. Alternatively, such excess unfilled or lightly filled hardenable or hardened dental composition can typically be removed within a few days by brushing. In another alternative, such excess unfilled or lightly filled hardenable or hardened dental composition can remain on the tooth as, for example, a sealant that can preferably provide additional protection to the tooth structure. Further, the compressible material can aid in keeping together pieces of a bracket that fractures upon debonding (e.g., a ceramic bracket).

DEFINITIONS

As used herein, "dental composition" refers to a material (e.g., a dental or orthodontic material) capable of adhering (e.g., bonding) to a tooth structure. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives, liners, sealants (e.g., orthodontic sealants), and coatings. Oftentimes a dental composition can be used to bond a dental article to a tooth structure.

As used herein, "excess" dental composition (e.g., excess adhesive) refers to unneeded dental composition at or near the periphery of the dental article after the dental article has been fully expressed on the tooth structure, and is often called flash.

As used herein, "dental article" refers to an article that can be adhered (e.g., bonded) to a tooth structure. Dental articles include, for example, crowns, bridges, veneers, inlays, onlays, fillings, orthodontic appliances, and prostheses (e.g., partial or full dentures).

As used herein, "orthodontic appliance" refers to any device intended to be bonded to a tooth structure for use in orthodontic treatment, including, but not limited to, orthodontic brackets, buccal tubes, lingual retainers, sheaths, orthodontic bands, bite openers, buttons, and cleats. The appliance has a base for receiving adhesive. Optionally, the base comprises a flange. The base can be made of metal, plastic, ceramic, crystalline, or combinations thereof, such as described in U.S. Pat. No. 5,522,725 (Jordan et al.), U.S. Pat. No. 5,439,379 (Hansen et al.), U.S. Pat. No. 5,746,594 (Jordan et al.), U.S. Pat. No. 6,280,185 (Palmer et al.) and U.S. Pat. No. 6,733,285 (Puttler et al.) and in published U.S. Patent Application No. 2009/0017411 (Pospisil et al.). Useful bases can include, for example, machined bases, molded bases, and/or a mesh bases. In certain embodiments, the base can be a custom base formed from cured adhesive layer(s) (i.e., single or multi-layer adhesives).

As used herein, a "packaged" article refers to an orthodontic appliance or card that is received in a container. Preferably, the container provides protection from environmental conditions including, for example, moisture and light.

As used herein, a "release" substrate refers to a substrate in contact with an article that is removed from the article before or during use of the article.

As used herein, "tooth structure" refers to surfaces including, for example, natural and artificial tooth surfaces, ceramic surfaces, veneers, bone, tooth models, and the like. Artificial tooth surfaces can be in the form of, for example, a crown, a bridge, a partial denture, or a pontic.

As used herein, a "layer" refers to a discontinuous (e.g., a patterned layer) or continuous (e.g., non-patterned) material extending across all or a portion of a material different than the layer. The layer may be of uniform or varying thickness.

As used herein, a "multi-layer" adhesive refers to an adhesive having two or more distinctly different layers (i.e., layers differing in composition, and preferably having different chemical and/or physical properties).

As used herein, a "patterned layer" refers to a discontinuous material extending across (and optionally attached to) only selected portions of a material different than the patterned layer.

As used herein, a "non-patterned layer" refers to a continuous material extending across (and optionally attached to) an entire portion of a material different than the non-patterned layer.

In general, a layer "on," "extending across," or "attached to" another material different than the layer is intended to be broadly interpreted to optionally include one or more additional layers between the layer and the material different than the layer.

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization. In another alternative, two or more parts can be provided as separate layers that initiate polymerization at the interface (e.g., spontaneously or upon application of shear stress) with no or partial mixing.

As used herein, "hardened" refers to a material or composition that has been cured (e.g., polymerized or crosslinked) or solidified.

As used herein, "hardener" refers to something that initiates hardening of a resin. A hardener may include, for example, a polymerization initiator system, a photoinitiator system, and/or a redox initiator system (e.g., including dual cure systems).

As used herein, "photobleachable" refers to loss of color upon exposure to actinic radiation.

As used herein, the term "(meth)acrylate" is a shorthand reference to acrylate, methacrylate, or combinations thereof, and "(meth)acrylic" is a shorthand reference to acrylic, methacrylic, or combinations thereof.

As used herein, the chemical term "group" allows for substitution. As used herein, "a" or "an" means one or more.

BRIEF DESCRIPTION OF THE FIGURES

FIG. 7 is an enlarged side cross-sectional view showing the act of applying a dental appliance to a patient's tooth using a placement device used with an indirect bonding method.

DETAILED DESCRIPTION OF ILLUSTRATIVE EMBODIMENTS

Figure 1:
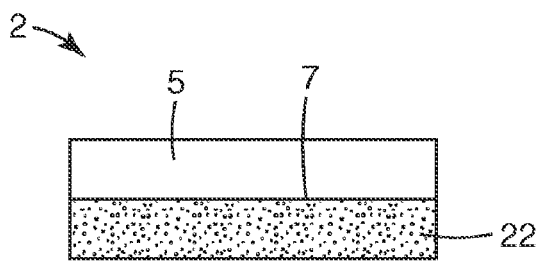
FIG. 1 is a side view of one embodiment of the present invention illustrating a dental article having a compressible material attached to a surface thereof.

Assemblies, kits, and methods as described herein include a compressible material that can fill the gap between the surface of a dental article (e.g., the base of an orthodontic appliance) and a tooth structure. Assemblies, kits, and methods as described herein optionally include the combination of the compressible material and a hardenable dental composition that can advantageously be unfilled or lightly filled. The combination of the compressible material and the unfilled or lightly filled hardenable dental composition can provide adequate handling properties for application and adequate adhesive properties upon hardening, while allowing for simplified removal, if desired, of excess dental composition by the practitioner. Alternatively, such excess unfilled or lightly filled hardenable or hardened dental composition can typically be removed within a few days by brushing.

Assemblies, kits, and methods of the present invention include a compressible material that becomes a part of the bond upon applying the dental article to a tooth structure and hardening a hardenable dental composition. As used herein, a "compressible material" is a material that is reduced in volume upon application of pressures typically employed to place and/or position a dental article on a tooth structure. Forces typically employed to place and/or position a dental article on a tooth structure are 0.5 to 5 pound-force applied to a bonding base of area 0.0164 square inch, corresponding to calculated pressures of 0.2 to 2.0 MPa. The ratio of the compressed volume/initial volume (i.e., compressibility) will vary depending on the compressible material used. However, the compressibility is typically 0.9 to 0.001, in certain embodiments 0.7 to 0.01, and in other certain embodiments 0.5 to 0.1.

As used herein, compressible materials can include elastic and/or inelastic materials. Elastic compressible materials include materials that substantially rebound (e.g., rebound to at least to 99% of the initial volume), preferably within 30 seconds at, for example, room temperature or oral temperature, after release of the pressure used to compress the material. Examples of elastic compressible materials include, but are not limited to, polymeric foams, elastic scrims, elastic nonwovens, and combinations thereof.

Inelastic compressible materials are materials that do not substantially rebound, i.e., rebound to at most 50%, in certain embodiments at most 25%, 10%, or even 5% of the initial volume, preferably within 30 seconds at, for example, room temperature or oral temperature, after release of the pressure used to compress the material. Examples of inelastic compressible materials include, but are not limited to, brittle materials (e.g., crosslinked polymeric foams, glass bubbles, glass fibers, ceramic fibers, and combinations thereof) and other materials having no rebound (e.g., dead-soft materials, i.e., the most soft and malleable state of a material). Examples of materials having substantially no rebound include, but are not limited to, foams having substantially no rebound, fibers and/or fiber mats having substantially no rebound, materials having voids in which the voids are at least partially collapsed upon compression (e.g., collapsible honeycomb structures made from paper, polymers, and/or polymeric foams), fabric knit structures, and combinations thereof. For some embodiments, an inelastic compressible material can be advantageous in that the pressure used to compress the compressible material need not be maintained after the dental article is placed and/or positioned on the tooth structure (e.g., prior to and/or during hardening and/or curing of the dental composition).

A wide variety of compressible materials can be used in assemblies, kits, and methods of the present invention, including, for example, porous materials, foamed materials, and materials including capsules. The compressible material can be a hydrophilic material, a hydrophobic material, or combinations thereof. The compressible material can be any color, with white or off-white colored compressible materials being preferred for certain embodiments. In certain embodiments, an opaque or colored compressible material can aid in visualization of any material remaining on the tooth surface after the appliance has been removed. The compressible material can be of uniform on non-uniform thickness. The compressible material can be in the form of a layer (e.g., a single layer or multi-layer). Multi-layer compressible materials can include layers that are the same and/or layers that differ from one another.

Assemblies including a compressible material can further include additional components in contact with the compressible material. For example, the assembly can further include a water scavenger (e.g., precipitated silica and/or molecular sieves) in contact with the compressible material to enhance water tolerance during use. For another example, the assembly can further include filler (e.g., fluoroaluminosilicate glass particulates) in contact with (e.g., embedded in or bonded to) the compressible material to modify physical and adhesive characteristics of the compressible material.

In some embodiments, the compressible material is or includes a foamed, hardenable dental composition that is optionally partially hardened, such as a dental adhesive or primer. For example, methacrylate-containing hardenable dental compositions can be foamed using hydrocarbon blowing agents (e.g., propane, isobutane, or combinations thereof such as a 1:1 mixture by weight of propane and isobutane).

For embodiments in which the compressible material is a porous material, a wide variety of porous materials can be used in assemblies, kits, and methods of the present invention. As used herein, a "porous material" is a material that includes pores (e.g., voids and/or vessels). In preferred embodiments, the pores are in communication with one another such that a material contained therein (e.g., a hardenable dental composition) can pass between pores (e.g., percolate), for example, during compression of the porous material. In such embodiments, the surface energy of the porous material and the hardenable dental composition can be selected, for example, to have small differences, such that the hardenable dental composition can wet out the compressible material to aid in the retention of the hardenable dental composition in the porous material prior to hardening, and to provide for enhanced mechanical properties and hydrolytic stability.

Exemplary porous materials include foams (e.g., polymeric foams including, for example, cellulose foams, glass foams, polymeric foams, and combinations thereof), sponges, nonwoven fabrics, glass fibers (e.g., glass wool), ceramic fibers, cotton fibers, cellulose fibers, woven mats, nonwoven mats, scrims, and combinations thereof. Exemplary materials are described, for example, in U.S. Pat. No. 4,605,402 (Iskra), U.S. Pat. No. 4,865,596 (Weisman et al.), U.S. Pat. No. 5,614,570 (Hansen et al.), U.S. Pat. No. 6,027,795 (Kabra et al.), U.S. Pat. No. 6,645,618 (Hobbs et al.); Japanese Patent No. JP63170437 (Sakadou et al.); and Nacht et al., "The microsponge: a novel topical programmable delivery system," in *Topical Drug Delivery Formulations*, D. W. Osborn and A. H. Amman (Eds.), Marel Dekker, New York, pp. 299-325 (1990).

For embodiments in which the compressible material includes fibers, the fibers can optionally be tied together (e.g., using a reactive silane, a curable resin, or a colloidal silica) to form a mat or scrim. In certain embodiments, mats can be prepared, for example, using short chopped glass or other fiber loosely bound. Optionally, the fibers can be temporarily encapsulated into a sheet or web to aid in cutting and handling using, for example, a water soluble or dispersible encapsulant (e.g., polyvinyl alcohol). In such embodiments, the mat can be cut into a desired shape and attached to an outer surface of a bracket, and the temporary encapsulant can then be washed away. In certain embodiments, nonwoven structures can be used as carriers for loading a reinforcing material (e.g., short chopped fibers) to enhance the strength of the composite formed upon curing.

In certain embodiments, the compressible material can include fibers that include all or a portion of a hardenable dental composition (e.g., fluoroaluminosilicate glass fiber).

Polymeric foams can include open-celled foams as described, for example, in U.S. Pat. No. 5,770,636 (Wernsing et al.) and U.S. Pat. No. 5,817,704 (Shively et al.); closed-celled foams as described, for example, in Westerman et al., *British Journal of Sports Medicine,* 36:205-208 (2002); or combinations thereof. Alternatively, closed-cell foams may be converted into porous fibrous articles if oriented and microfibrillated as described, for example, in U.S. Pat. No. 6,645,618 (Hobbs et al.). The hydrophilic/lipophilic balance at the surface of the foam structure can be modified, for example, using polyelectrolytes or functionalized particles during preparation as described, for example, in U.S. Pat. No. 6,750,261 (Clear et al.). In some embodiments, the foam can be surface modified by thermal, chemical (e.g., acid-etching, corona treatment, plasma etching, glow discharge, or flame treatment), and/or photochemical (e.g., ultraviolet irradiation) means.

In certain embodiments, the polymeric foam has a void volume of at least 50 volume %, preferably at least 70 volume %, more preferably at least 85 volume %, and even more preferably at least 95 volume %. In certain embodiments, the polymeric foam has a void volume of at most 99.9 volume %, preferably at most 99.5 volume %, more preferably at most 99 volume %, and even more preferably at most 98 volume %. For polymeric foams in which the bulk density of the polymer is typically near 1, foam densities can be closely correlated with void volumes.

In certain preferred embodiments, an assembly can further include a hardenable dental composition at least partially within the pores of a porous material. For such embodiments, at least 80 volume %, preferably at least 90 volume %, and more preferably 100 volume % of the void volume is filled with the hardenable dental composition.

For certain embodiments in which the compressible material is a porous foam (e.g., cellulose foams, glass foams, ceramic foams, polymeric foams, and combinations thereof), the foam can be prepared by a wide variety of methods known in the art. For example, porous foams can be prepared by incorporating one or more foaming agents into a material and activating the foaming agent(s). Foaming agents, also called blowing agents, can be used to foam plastics, rubbers, and thermoset resins to impart a cellular structure to the material. Chemical foaming agents form cells by decomposing to release gas when heated to their activation temperature. Physical blowing agents, on the other hand, are usually liquids at room temperature that volatilize when heated. Foams can also be prepared by dispersing bubbles or hollow capsules into the material, or using microspheres that encapsulate a physical blowing agent and expand into bubbles when heated. Alternatively, open-celled foams can be made by mixing a water-in-oil emulsion, either thermally or chemically polymerizing the oil phase, and then removing the water. For certain embodiments in which the compressible material is a porous foam, the porous foam can be prepared by foaming and optionally at least partially hardening a hardenable dental composition. For example, methacrylate-containing hardenable dental compositions can be foamed using hydrocarbon blowing agents (e.g., propane, isobutane, or combinations thereof such as a 1:1 mixture by weight of propane and isobutane).

For embodiments in which the compressible material includes capsules, the capsules are preferably hollow and can be ruptured by ordinary pressure encountered during application of the dental appliance to a tooth structure. Optionally, an assembly including capsules can further include a hardenable dental composition at least partially on an outer surface of the capsules. Optionally, an assembly including hollow capsules can further include a hardenable dental composition located at least partially within the capsules. Optionally, an assembly including hollow capsules can further include a liquid (e.g., aqueous or non-aqueous) inside at least a portion of the capsules. For example, an assembly including hollow capsules can further include water inside at least a portion of the capsules, which could be released when capsules are broken upon compression. Release of water upon compression could be useful for example, if the compressible material includes a water soluble or dispersible material (e.g., polyacrylic acid) that can be beneficial upon dissolution and/or dispersion. The release of water may also start an acid-base hardening reaction. Alternatively, the capsules may contain one half of a redox pair and begin the hardening reaction upon release. A wide variety of capsules can be used including, for example, microcapsules (i.e., capsules that typically have a diameter less than 10 micrometers), hollow glass beads (e.g., glass bubbles), hollow plastic beads, ceramic bubbles, and combinations thereof. Exemplary materials are disclosed, for example, in U.S. Pat. No. 4,303,730 (Torobin), U.S. Pat. No. 4,336,338 (Downs et al.), U.S. Pat. No. 5,045,569 (Delgado), and U.S. Pat. No. 5,861,214 (Kitano et al.).

In certain embodiment, assemblies, kits, and methods of the present invention include a dental article and a compressible material. In certain embodiments, the assembly includes a layer of compressible material attached to a surface of the dental article. Dental articles having a compressible material attached to a surface thereof are to be distinguished from dental articles (e.g., precoated orthodontic appliances) having a release substrate (e.g., a release liner) on the precoated adhesive. In contrast to release substrates, which are designed to be removed before or during use of the article, a compressible material that is attached to a surface of a dental article is designed to remain on the dental article during use of the article, and in fact becomes a part of the bond upon applying the dental article and a hardenable dental composition to a tooth structure, and hardening the hardenable dental composition.

For some embodiments of assemblies, kits, and methods of the present invention that include a dental article having an outer surface and a compressible material, the compressible material can be of such size and shape that the compressible material can form a continuous layer on the outer surface of the article. For alternative embodiments, the compressible material can be of such size and shape that it can form a discontinuous layer (e.g., a center hole) on the surface of the article.

The compressible material can form a layer having an area larger than the outer surface of the article, coextensive with the outer surface of the article, or smaller than the outer surface of the article. For certain embodiments, a layer having an area smaller than the outer surface of the article can be advantageously arranged on the outer surface of the article to prevent the compressible material from extending beyond the outer surface of the article upon compression.

The compressible material can optionally include two or more different materials that can be arranged as desired. For example, in certain embodiments, a mat or scrim can be made of two or more different types of fibers, wherein each type of fiber is distributed throughout the mat or scrim. In other embodiments, a mat or scrim can be made of two or more different types of fibers, wherein each type of fiber is not distributed throughout the mat or scrim. For example, one type of fiber can be substantially located in one layer (e.g., to form a denser material on the side adjacent the outer surface of the article) and another type of fiber can be substantially located in another layer (e.g., to form a loftier material on the side adjacent the tooth surface). For another example, one type of fiber can be substantially located proximate the periphery of the mat or scrim (e.g., to form a denser material and/or to seal the edges of the compressible material), and another type of fiber can be substantially located proximate the center of the mat or scrim (e.g., to form a loftier material). For certain embodiments, different mats or scrims can be used for different teeth. For example, the mats or scrims used for molars may be loftier than the mats or scrims used for incisors. In certain embodiments, two or more appliances with different mats or scrims intended for use on different teeth can be combined in a single package similar to that described, for example, in U.S. Patent Application Publication No. 2006/0207893 (Cinader et al.).

In certain embodiments, a compressible material (e.g., a mat) can be built in situ on the outer surface of the article. For example, a perimeter containment can be placed proximate the periphery of the outer surface. Reinforcement, such as short chopped glass fibers, can be placed within the perimeter containment and bound with a heat or light curable binder, which can be precoated on the fiber, or introduced simultaneously (i.e. sprayed) or subsequent to placement of the fiber. Such a compressible material can be tailored to allow the mat to properly compress during bonding to the tooth surface. Optionally, a tooling element can be used to form the outer surface of the mat into an optimum contour, particularly for use with highly curved tooth surfaces.

An exemplary embodiment for a dental article having a compressible material attached to the base thereof is illustrated in FIG. 1. In FIG. 1, exemplary assembly 2 includes dental article 5 having surface 7 for bonding to a tooth structure. Exemplary article 5 can represent a wide variety of dental articles including, but not limited to, crowns, bridges, veneers, inlays, onlays, fillings, orthodontic appliances and devices, and prostheses (e.g., partial or full dentures). Exemplary assembly 2 further includes compressible material 22 attached to surface 7 of dental article 5.

In the exemplary embodiment illustrated in FIG. 1, compressible material 22 extends across surface 7 of dental article 5. Compressible material 22 in combination with a hardenable dental composition can serve in whole or at least in part to securely fix article 2 to a tooth structure by a bond having sufficient strength to resist unintended detachment from the tooth structure. Optionally, all or a portion of a hardenable dental composition is in contact with the compressible material 22. A hardenable dental composition can be applied to all or a portion of compressible material 22 by methods known in the art including, but not limited to, coating, spraying, dipping, brushing, and the like. A hardenable dental composition can be applied to compressible material 22 substantially uniformly or non-uniformly (e.g., applied to only one side of the compressible material). A hardenable dental composition can be patterned on compressible material 22. For example, an unfilled or lightly filled hardenable dental composition can be applied proximate the periphery of compressible material 22, and a filled hardenable dental composition can be applied proximate the center of compressible material 22. In some embodiments, one part of a two-part hardenable dental composition (e.g., a chemical cure primer) can be applied to all or a portion of compressible material 22, and the second part of the two-part hardenable dental composition can be applied to a tooth surface. In other embodiments, one part of a redox pair can be coated on, adsorbed by, and/or embedded in compressible material 22, and the other part of the redox pair can be included in the hardenable dental composition, which in preferred embodiments is applied just prior to placement on the tooth.

In certain embodiments, compressible material 22 is supplied by the manufacturer separately from dental article 5, and the practitioner can attach compressible material 22 to surface 7 of dental article 5. In other embodiments, compressible material 22 is attached by the manufacturer to surface 7 of dental article 5. In certain embodiments, compressible material 22 can be attached to surface 7 of dental article 5 using an unhardened dental composition, a partially hardened dental composition, or a hardened dental composition.

In preferred embodiments, compressible material 22 is mechanically bonded to surface 7 of dental article 5, chemically bonded to surface 7 of dental article 5, or a combination thereof. As used herein, "mechanically bonded" means bonded or attached through physical means (e.g., using hooks, loops, protrusions, van der Waals interactions, ionic bonds, and the like, including combinations thereof), and in certain embodiments utilizing the undercuts provided by mesh (e.g., on Victory Series brackets) and glass grit (e.g., on ceramic brackets). As used herein, "chemically bonded" means bonded or attached through chemical means (e.g., via shared electron pairs such as covalent bonding, coordinate covalent bonding, acid-base interactions such as Brønsted-Lowry reactions, and the like, including combinations thereof). For example, a hardenable dental composition (e.g., a hardenable resin, glass ionomer, resin-modified glass ionomer, and/or epoxy) can be hardened to chemically bond the compressible material 22 to surface 7 of dental article 5. In certain embodiments, compressible material 22 can be surface treated (e.g., with a silane coupling agent) to enhance the bond to surface 7 of dental article 5. In some embodiments, the compressible material 22 can be bonded to surface 7 of dental article 5 by melting or softening the compressible material.

In certain embodiments, attachment of compressible material 22 to surface 7 of dental article 5 can be enhanced by a sandblasting treatment as described, for example, in Akin-Nergiz et al., *Fortschritte der Kieferorthopädie* (1995) 56(1):49-55; Atsu et al., *Angle Orthodontist* (2006) 76(5): 857-862; Mujagic et al., *J. of Clinical Orthodontics* (2005) 39(6):375-382; Newman et al., *American J. of Orthodontics and Dentofacial Orthopedics* (1995) 108(3):237-241; and Wiechmann, *J. of Orofacial Orthopedics* (2000) 61(4):280-291. In brief, the treatment includes sandblasting surface 7 with a silica-coated alumina sandblasting medium available under the trade designation Rocatec Plus from 3M, St. Paul, Minn. The sandblasting treatment can be carried out using, for example, a blasting module available under the trade designation Rocatec Jr. from 3M, St. Paul, Minn., with the module set at 2.8 bar for 2 to 3 seconds at a distance of one centimeter. A solution of silane (e.g., a silane in ethanol available under the trade designation 3M ESPE Sil from 3M, St. Paul, Minn.) can then be applied to treated surface 7 and allowed to dry at room temperature for at least 5 minutes. It is believed that the silane can further enhance the bonding of methacrylate-containing resins to treated surface 7.

In one embodiment, compressible material 22 is supplied having a hardenable dental composition therein. For embodiments in which compressible material 22 is attached by the manufacturer to surface 7 of dental article 5 and supplied having a hardenable dental composition therein, it may be preferred to supply the article as a packaged article, as described herein. In another embodiment, a hardenable dental composition can be added to the compressible material by a practitioner. For example, the practitioner can apply a hardenable dental composition to compressible material 22, or compressible material 22 can be dipped or immersed in a hardenable dental composition.

It should be understood that assembly 2 can optionally include additional layer(s) of dental compositions (e.g., orthodontic adhesives, orthodontic primers, or combinations thereof, which are not illustrated in FIG. 1) in contact with compressible material 22. Specifically, such additional layer(s) can be between surface 7 and compressible material 22; on compressible material 22 opposite surface 7; or both. Such layers may or may not cover the same area, and may independently be discontinuous (e.g., a patterned layer) or continuous (e.g., non-patterned) materials extending across all or a portion of compressible material 22. For embodiments in which such an additional layer (e.g., an unhardened, partially hardened, or hardened layer) is present between surface 7 and compressible material 22, the layer may be used, for example, to adhere the compressible material 22 to surface 7.

Figure 2:
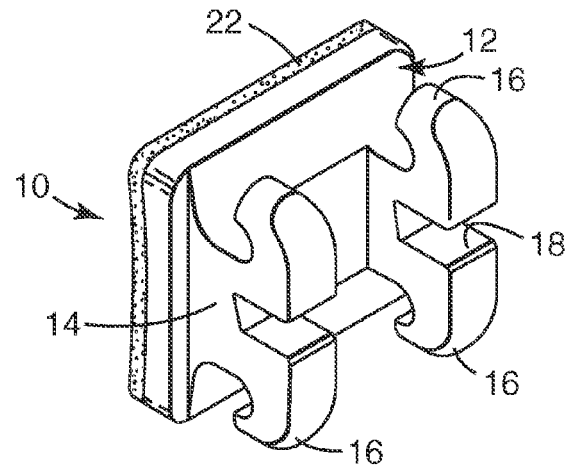
FIG. 2 is perspective view of a preferred embodiment of the present invention illustrating an orthodontic appliance having a compressible material attached to the base thereof.
Figure 3:
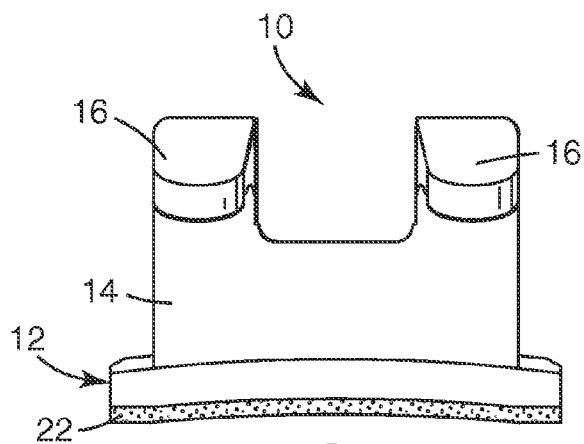
FIG. 3 is a side view of the orthodontic appliance of FIG. 2.

An exemplary embodiment of an assembly that includes an orthodontic appliance having a compressible material attached to the base thereof is illustrated in FIGS. 2 and 3. In FIGS. 2 and 3, an exemplary orthodontic appliance is designated by the numeral 10 and is a bracket, although other appliances such as buccal tubes, buttons, sheaths, bite openers, lingual retainers, bands, cleats, and other attachments are also possible. Appliance 10 includes a base 12. Appliance 10 also has a body 14 that extends outwardly from base 12. Base 12 can be a flange made of metal, plastic, glass, ceramic, or combinations thereof. Base 12 can include a mesh-like structure, such as a fine wire screen. Base 12 can include particles (such as shards, grit, spheres, or other structure that optionally includes undercuts). Alternatively, base 12 can be a custom base formed from one or more at least partially hardened dental composition layer(s). Tiewings 16 are connected to body 14, and archwire slot 18 extends through a space between tiewings 16. Base 12, body 14, and tiewings 16 may be made of any one of a number of materials suitable for use in the oral cavity and having sufficient strength to withstand the correction forces applied during treatment. Suitable materials include, for example, metallic materials (such as stainless steel), ceramic materials (such as monocrystalline or polycrystalline alumina), and plastic materials (such as fiber-reinforced polycarbonate). Optionally, base 12, body 14, and tiewings 16 are integrally made as a unitary component.

In the exemplary embodiment illustrated in FIGS. 2 and 3, compressible material 22 extends across base 12 of appliance 10. Compressible material 22 in combination with a hardenable dental composition can serve in whole or at least in part to securely fix appliance 10 to the patient's tooth by a bond having sufficient strength to resist unintended detachment from the tooth during the course of treatment.

In one embodiment, compressible material 22 is attached by the manufacturer to base 12 of appliance 10. In preferred embodiments, compressible material 22 is mechanically bonded to base 12 of appliance 10, chemically bonded to base 12 of appliance 10, or a combination thereof.

Optionally, the manufacturer or supplier of the appliance 10 provides a hardenable dental composition in contact with the compressible material 22. In one embodiment, compressible material 22 is supplied having a hardenable dental composition therein. For embodiments in which compressible material 22 is attached by the manufacturer to base 12 of appliance 10 and supplied as an assembly having a hardenable dental composition therein, it may be preferred to supply the assembly in a package or container that includes the article, as described herein. Exemplary containers are well known in the art and are disclosed, for example, in U.S. Pat. No. 5,172,809 (Jacobs et al.) and U.S. Pat. No. 6,089,861 (Kelly et al.). In certain embodiments, the package can be an inverted blister with a foam inside that contacts the tie wings such that the appliance would be held in place and not slide on the liner. For example, rather than contacting the "bottom" of the blister well, the appliance can be positioned in the package such that it rests on the lid, and foam can be placed in the bottom of the blister such that it contacts the tie wings and holds the bracket in place. In another embodiment, a hardenable dental composition can be added to the compressible material by a practitioner. For example, the practitioner can apply a hardenable dental composition to compressible material 22, or compressible material 22 can be dipped or immersed in a hardenable dental composition.

The external surface of the compressible material 22 optionally has a concave configuration, and optionally has a compound concave configuration, that inversely matches the convex configuration of the outer surface of the tooth intended for use with the appliance 10. As one example, the compressible material 22 may have a generally uniform thickness and the outer surface of the base 12 may have a concave configuration, such that the external surface of the compressible material when attached to the outer surface of the base 12 has a concave configuration that generally matches of the concave configuration of the outer surface of the base 12. As another example, the outer surface of the base 12 may have a generally planar configuration that matches a generally planar configuration of a facing surface of the compressible material 22, while the external surface of the compressible material 22 may have a concave configuration that inversely matches the convex configuration of the tooth surface. Other constructions are also possible, including, for example, constructions in which the thickness of compressible material 22 varies corresponding to different position of the base.

It should be understood that the assembly comprising the orthodontic appliance 10 can optionally include additional layer(s) of dental compositions (e.g., orthodontic adhesives, orthodontic primers, or combinations thereof, which are not illustrated in FIGS. 2 and 3) in contact with compressible material 22. Specifically, such additional layer(s) can be between base 12 and compressible material 22; on compressible material 22 opposite base 12; or both. Such layers may or may not cover the same area, and may independently be discontinuous (e.g., a patterned layer) or continuous (e.g., non-patterned) materials extending across all or a portion of compressible material 22.

Figure 4:
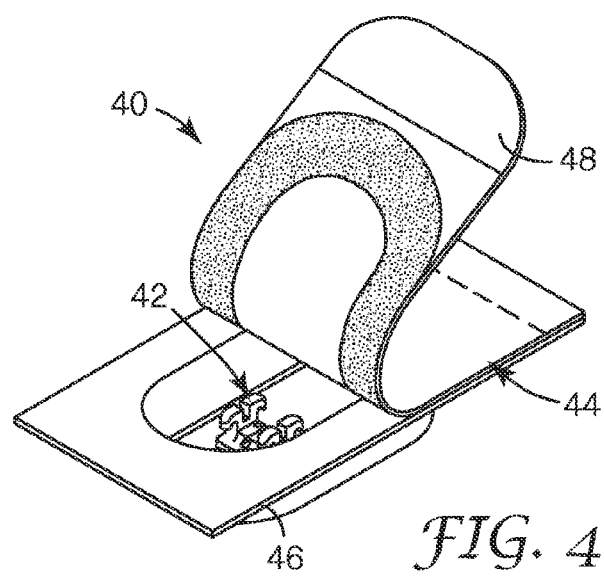
FIG. 4 is perspective view of a certain embodiment of the present invention illustrating a packaged article including an orthodontic appliance having a compressible material attached to the base thereof in a container in which the cover has been partially opened.

Referring to FIG. 4, an exemplary embodiment of packaged assembly 40 is shown including assembly 42, which can include an orthodontic appliance that is the same or different than the exemplary embodiment illustrated in FIGS. 2 and 3. Package 44 includes container 46 and cover 48. Cover 48, which is releasably connected to container 46 as initially provided, is peeled from container 46 to open the package for removal of assembly 42. In FIG. 4, cover 48 has been peeled back from container 46 to partially open package 44.

In preferred embodiments, the package provides excellent protection against degradation of optional hardenable dental composition(s) (e.g., photocurable materials), even after extended periods of time. Such containers are particularly useful for embodiments in which the optional hardenable dental composition optionally includes dyes that impart a color changing feature to the adhesive. Such containers preferably effectively block the passage of actinic radiation over a broad spectral range, and as a result, the optional dental compositions do not prematurely lose color during storage.

In preferred embodiments, the package includes container 46 comprising a polymer and metallic particles. As an example, container 46 may be made of polypropylene that is compounded with aluminum filler or receives an aluminum powder coating as disclosed, for example, in U.S. Pat. Application Publication No. 2003/0196914 A1 (Tzou et al.). The combination of polymer and metallic particles provides a highly effective block to the passage of actinic radiation to color changing dyes, even though such dyes are known to be highly sensitive to light. Such containers also exhibit good vapor barrier properties. As a result, the rheological characteristics of the hardenable dental composition(s) are less likely to change over extended periods of time. For example, the improved vapor barrier properties of such containers provide substantial protection against degradation of the handling characteristics of adhesives so that the dental compositions do not prematurely cure or dry or become otherwise unsatisfactory. Suitable covers 48 for such containers can be made of any material that is substantially opaque to the transmission of actinic radiation so that the dental compositions do not prematurely cure. Examples of suitable materials for cover 48 include laminates of aluminum foil and polymers. For example, the laminate may comprise a layer of polyethyleneterephthalate, adhesive, aluminum foil, adhesive and oriented polypropylene.

In some embodiments, a packaged assembly including an orthodontic appliance, a compressible material, and a hardenable dental composition may further include a release substrate as described, for example, in U.S. Pat. No. 6,183,249 (Brennan et al.).

In some embodiments, a package can include a set of assemblies including orthodontic appliances, wherein at least one of the assemblies includes an appliance having a compressible material thereon. Additional examples of assemblies (e.g., appliances) and sets of assemblies are described in U.S. Pat. Application Publication No. 2005/0133384 A1 (Cinader et al.). Packaged assemblies (e.g., orthodontic appliances) are described, for example, in U.S. Pat. Application Publication No. 2003/0196914 A1 (Tzou et al.) and U.S. Pat. No. 4,978,007 (Jacobs et al.), U.S. Pat. No. 5,015,180 (Randklev), U.S. Pat. No. 5,328,363 (Chester et al.), and U.S. Pat. No. 6,183,249 (Brennan et al.).

Dental Compositions

Hardenable dental compositions useful in assemblies, kits, and methods of the present invention typically include one or more hardenable components and a hardener. Optionally, hardenable dental compositions as described herein can include, for example, an initiator system, an ethylenically unsaturated compound, and/or one or more fillers. Hardenable and hardened dental compositions as described herein can be used for a variety of dental and orthodontic applications that utilize a material capable of adhering (e.g., bonding) to a tooth structure. Uses for such hardenable and hardened dental compositions include, for example, uses as adhesives (e.g., dental and/or orthodontic adhesives), cements (e.g., glass ionomer cements, resin-modified glass ionomer cements, and orthodontic cements), primers (e.g., orthodontic primers), restoratives, liners, sealants (e.g., orthodontic sealants), coatings, and combinations thereof.

Hardenable dental compositions (e.g., hardenable dental compositions) as described herein typically include a hardenable (e.g., polymerizable) component, thereby forming hardenable (e.g., polymerizable) compositions. The hardenable component can include a wide variety of chemistries, such as ethylenically unsaturated compounds (with or without acid functionality), epoxy (oxirane) resins, vinyl ethers, photopolymerization systems, redox cure systems, glass ionomer cements, polyethers, polysiloxanes, and the like. In some embodiments, the dental compositions can be hardened (e.g., polymerized by conventional photopolymerization and/or chemical polymerization techniques) prior to applying the hardened dental composition. In other embodiments, a dental composition can be hardened (e.g., polymerized by conventional photopolymerization and/or chemical polymerization techniques) after applying the hardenable dental composition.

In certain embodiments, the dental compositions are photopolymerizable, i.e., the dental compositions contain a photoinitiator (i.e., a photoinitiator system) that upon irradiation with actinic radiation initiates the polymerization (or hardening) of the dental composition. Such photopolymerizable compositions can be free radically polymerizable or cationically polymerizable. In other embodiments, the dental compositions are chemically hardenable, i.e., the dental compositions contain a chemical initiator (i.e., initiator system) that can polymerize, cure, or otherwise harden the dental composition without dependence on irradiation with actinic radiation. Such chemically hardenable dental compositions are sometimes referred to as "self-cure" compositions and may include glass ionomer cements (e.g., conventional and resin-modified glass ionomer cements), redox cure systems, and combinations thereof.

Suitable photopolymerizable components that can be used in the dental compositions as disclosed herein include, for example, epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional acrylates, epoxy-functional methacrylates, and combinations thereof.

Ethylenically Unsaturated Compounds

Dental compositions as disclosed herein may include one or more hardenable components in the form of ethylenically unsaturated compounds with or without acid functionality, thereby forming hardenable dental compositions.

Suitable hardenable dental compositions may include hardenable components (e.g., photopolymerizable compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

The dental compositions (e.g., photopolymerizable compositions) may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl(meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The hardenable component may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments hardenable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the hardenable components can be used if desired.

Preferably dental compositions as disclosed herein include at least 5% by weight, preferably at least 10% by weight, and more preferably at least 15% by weight ethylenically unsaturated compounds (e.g., with and/or without acid functionality), based on the total weight of the unfilled composition. Certain dental compositions as disclosed herein (e.g., unfilled dental compositions that consist of one or more ethylenically unsaturated compounds and an initiator system) can include 99% by weight or even higher of ethylenically unsaturated compounds (e.g., with and/or without acid functionality), based on the total weight of the unfilled composition. Other certain dental compositions as disclosed herein include at most 99% by weight, preferably at most 98% by weight, and more preferably at most 95% by weight ethylenically unsaturated compounds (e.g., with and/or without acid functionality), based on the total weight of the unfilled composition.

Ethylenically Unsaturated Compounds with Acid Functionality

Dental compositions as disclosed herein may include one or more hardenable components in the form of ethylenically unsaturated compounds with acid functionality, thereby forming hardenable dental compositions.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis ((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)

acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain compositions for use in preferred methods of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Pat. Application Publication No. 2004/0206932 (Abuelyaman et al.); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Dental compositions as disclosed herein can also include compositions that include combinations of ethylenically unsaturated compounds with acid functionality. Preferably the dental compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler. Such compositions are described, for example, in Published U.S. Application No. 2007/0248927 (Luchterhandt et al.). See, also, U.S. Pat. No. 7,449,499 (Bradley et al.) and U.S. Pat. No. 7,452,924 (Aasen et al.); and Published U.S. Application Nos. 2005/0175966 (Falsafi et al.), 2009/0011388 (Bradley et al.), and 2009/0035728 (Aasen et al.).

Preferably dental compositions as disclosed herein include at least 5% by weight, preferably at least 10% by weight, and more preferably at least 15% by weight ethylenically unsaturated compounds with acid functionality, based on the total weight of the unfilled composition. Certain dental compositions as disclosed herein (e.g., unfilled dental compositions that consist of one or more ethylenically unsaturated compounds and an initiator system) can include 99% by weight or even higher of ethylenically unsaturated compounds with acid functionality, based on the total weight of the unfilled composition. Other certain dental compositions as disclosed herein include at most 99% by weight, preferably at most 98% by weight, and more preferably at most 95% by weight ethylenically unsaturated compounds with acid functionality, based on the total weight of the unfilled composition.

Epoxy (Oxirane) or Vinyl Ether Compounds

Hardenable dental compositions as disclosed herein may include one or more hardenable components in the form of epoxy (oxirane) compounds (which contain cationically active epoxy groups) or vinyl ether compounds (which contain cationically active vinyl ether groups), thereby forming hardenable dental compositions.

The epoxy or vinyl ether monomers can be used alone as the hardenable component in a dental composition or in combination with other monomer classes, e.g., ethylenically unsaturated compounds as described herein, and can include as part of their chemical structures aromatic groups, aliphatic groups, cycloaliphatic groups, and combinations thereof.

Examples of epoxy (oxirane) compounds include organic compounds having an oxirane ring that is polymerizable by ring opening. These materials include monomeric epoxy compounds and epoxides of the polymeric type and can be aliphatic, cycloaliphatic, aromatic or heterocyclic. These compounds generally have, on the average, at least 1 polymerizable epoxy group per molecule, in some embodiments at least 1.5, and in other embodiments at least 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, carbosilane groups, nitro groups, phosphate groups, and the like. The molecular weight of the epoxy-containing materials may vary from 58 to 100,000 or more.

Suitable epoxy-containing materials useful as the resin system reactive components for use in methods of the present invention are listed in U.S. Pat. No. 6,187,836 (Oxman et al.) and U.S. Pat. No. 6,084,004 (Weinmann et al.).

Other suitable epoxy resins useful as the resin system reactive components include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexyl-methyl) adipate. For a more detailed list of useful epoxides of this nature, reference is made to U.S. Pat. No. 6,245,828 (Weinmann et al.), U.S. Pat. No. 5,037,861 (Crivello et al), and U.S. Pat. No. 6,779,656 (Klettke et al.).

Other epoxy resins that may be useful in dental compositions as disclosed herein include glycidyl ether monomers. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)propane). Further examples of epoxides of this type are described in U.S. Pat. No. 3,018,262 (Schroeder), and in "Handbook of Epoxy Resins" by Lee and Neville, McGraw-Hill Book Co., New York (1967).

Other suitable epoxides useful as the resin system reactive components are those that contain silicon, useful examples of which are described in International Pat. Application Publication No. WO 01/51540 (Klettke et al.).

Additional suitable epoxides useful as the resin system reactive components include octadecylene oxide, epichlorohydrin, styrene oxide, vinyl cyclohexene oxide, glycidol, glycidylmethacrylate, diglycidyl ether of Bisphenol A and other commercially available epoxides, as provided in U.S. Pat. No. 7,262,228 (Oxman et al.).

Blends of various epoxy-containing materials are also contemplated. Examples of such blends include two or more weight average molecular weight distributions of epoxy-containing compounds, such as low molecular weight (below 200), intermediate molecular weight (200 to 10,000) and higher molecular weight (above 10,000). Alternatively or additionally, the epoxy resin may contain a blend of epoxy-containing materials having different chemical natures, such as aliphatic and aromatic, or functionalities, such as polar and non-polar.

Other types of useful hardenable components having cationically active functional groups include vinyl ethers, oxetanes, spiro-orthocarbonates, spiro-orthoesters, and the like.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the CYCLOMER series, such as CYCLOMER M-100, M-101, or A-200 available from Daicel Chemical, Japan, and EBECRYL-3605 available from Radcure Specialties, UCB Chemicals, Atlanta, Ga.

The cationically curable components may further include a hydroxyl-containing organic material. Suitable hydroxyl-containing materials may be any organic material having hydroxyl functionality of at least 1, and preferably at least 2. Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights (i.e., from 32 to 200), intermediate molecular weights (i.e., from 200 to 10,000, or high molecular weights (i.e., above 10,000). As used herein, all molecular weights are weight average molecular weights.

The hydroxyl-containing materials may be non-aromatic in nature or may contain aromatic functionality. The hydroxyl-containing material may optionally contain heteroatoms in the backbone of the molecule, such as nitrogen, oxygen, sulfur, and the like. The hydroxyl-containing material may, for example, be selected from naturally occurring or synthetically prepared cellulosic materials. The hydroxyl-containing material should be substantially free of groups which may be thermally or photolytically unstable; that is, the material should not decompose or liberate volatile components at temperatures below 100° C. or in the presence of actinic light which may be encountered during the desired photopolymerization conditions for the polymerizable compositions.

Suitable hydroxyl-containing materials useful in methods of the present invention are listed in U.S. Pat. No. 6,187,836 (Oxman et al.).

The hardenable component(s) may also contain hydroxyl groups and cationically active functional groups in a single molecule. An example is a single molecule that includes both hydroxyl groups and epoxy groups.

Glass Ionomers

Hardenable dental compositions as described herein may include glass ionomer cements such as conventional glass ionomer cements that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers (i.e., glass ionomer cements) typically are supplied in powder/liquid formulations that are mixed just before use. The mixture will undergo self-hardening in the dark due to an ionic reaction between the acidic repeating units of the polycarboxylic acid and cations leached from the glass.

The glass ionomer cements may also include resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of the acidic repeating units with pendent curable groups and a photoinitiator is added to provide a second cure mechanism, e.g., as described in U.S. Pat. No. 5,130,347 (Mitra). Acrylate or methacrylate groups are usually employed as the pendant curable group. In another type of RMGI, the cement includes a polycarboxylic acid, an acrylate or methacrylate-functional monomer and a photoinitiator, e.g., as in Mathis et al., "Properties of a New Glass Ionomer/Composite Resin Hybrid Restorative", Abstract No. 51, J. Dent Res., 66:113 (1987) and as in U.S. Pat. No. 5,063,257 (Akahane et al.), U.S. Pat. No. 5,520,725 (Kato et al.), U.S. Pat. No. 5,859,089 (Qian), U.S. Pat. No. 5,925,715 (Mitra), and U.S. Pat. No. 5,962,550 (Akahane et al.). In another type of RMGI, the cement may include a polycarboxylic acid, an acrylate or methacrylate-functional monomer, and a redox or other chemical cure system, e.g., as described in U.S. Pat. No. 5,154,762 (Mitra et al.), U.S. Pat. No. 5,520,725 (Kato et al.), and U.S. Pat. No. 5,871,360 (Kato). In another type of RMGI, the cement may include various monomer-containing or resin-containing components as described in U.S. Pat. No. 4,872,936 (Engelbrecht), U.S. Pat. No. 5,227,413 (Mitra), U.S. Pat. No. 5,367,002 (Huang et al.), and U.S. Pat. No. 5,965,632 (Orlowski). Dental compositions including such cements are able to harden in the dark due to the ionic reaction between the acidic repeating units of the polycarboxylic acid and cations leached from the glass, and commercial RMGI products typically also cure on exposure of the cement to light from a dental curing lamp. RMGI cements that contain a redox cure system and that can be cured in the dark without the use of actinic radiation are described in U.S. Pat. No. 6,765,038 (Mitra).

In certain embodiments, RMGI cements are formulated as powder/liquid or paste/paste systems, and contain water as mixed and applied. For embodiments in which the assembly includes a compressible material having the hardenable material applied thereto, water may be separated from the resin and filler. In other certain embodiments, cements having good shelf stability can be prepared by suspending water in the resin using an emulsifier to create a water-in-oil microemulsion. For other embodiments, in which the hardenable material contains no water, excess water present on the teeth can provide water for the bonding process. Fluoroaluminosilicate glass may be incorporated as an additional particulate filler or as a fibrous compressible material.

Photoinitiator Systems

In certain embodiments, the dental compositions of the present invention are photopolymerizable, i.e., the dental compositions contain a photopolymerizable component and a photoinitiator (i.e., a photoinitiator system) that upon irradiation with actinic radiation initiates the polymerization (or hardening) of the dental composition. Such photopolymerizable compositions can be free radically polymerizable or cationically polymerizable.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propane-dione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), U.S. Pat. No. 4,737,593 (Ellrich et al.), and U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the dental composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the dental composition. Useful amounts of other initiators are well known to those of skill in the art.

Suitable photoinitiators for polymerizing cationically photopolymerizable compositions include binary and tertiary systems. Typical tertiary photoinitiators include an iodonium salt, a photosensitizer, and an electron donor compound as described in EP 0 897 710 (Weinmann et al.); in U.S. Pat. No. 5,856,373 (Kaisaki et al.), U.S. Pat. No. 6,084,004 (Weinmann et al.), U.S. Pat. No. 6,187,833 (Oxman et al.), U.S. Pat. No. 6,187,836 (Oxman et al.); and U.S. Pat. No. 6,765,036 (Dede et al.). The dental compositions of the invention can include one or more anthracene-based compounds as electron donors. In some embodiments, the dental compositions comprise multiple substituted anthracene compounds or a combination of a substituted anthracene compound with unsubstituted anthracene. The combination of these mixed-anthracene electron donors as part of a photoinitiator system provides significantly enhanced cure depth and cure speed and temperature insensitivity when compared to comparable single-donor photoinitiator systems in the same matrix. Such compositions with anthracene-based electron donors are described in U.S. Pat. No. 7,262,228 (Oxman et al.).

Suitable iodonium salts include tolylcumyliodonium tetrakis(pentafluorophenyl)borate, tolylcumyliodonium tetrakis(3,5-bis(trifluoromethyl)-phenyl)borate, and the diaryl iodonium salts, e.g., diphenyliodonium chloride, diphenyliodonium hexafluorophosphate, diphenyliodonium hexafluoroantimonate, and diphenyliodonium tetrafluoroboarate. Suitable photosensitizers are monoketones and diketones that absorb some light within a range of 450 nm to 520 nm (preferably, 450 nm to 500 nm). More suitable compounds are alpha diketones that have some light absorption within a range of 450 nm to 520 nm (even more preferably, 450 nm to 500 nm). Preferred compounds are camphorquinone, benzil, furil, 3,3,6,6-tetramethylcyclohexanedione, phenanthraquinone and other cyclic alpha diketones. Most preferred is camphorquinone. Suitable electron donor compounds include substituted amines, e.g., ethyl 4-(dimethylamino)benzoate and 2-butoxyethyl 4-(dimethylamino)benzoate; and polycondensed aromatic compounds (e.g. anthracene).

The initiator system is present in an amount sufficient to provide the desired rate of hardening (e.g., polymerizing and/or crosslinking). For a photoinitiator, this amount will be dependent in part on the light source, the thickness of the layer to be exposed to radiant energy, and the extinction coefficient of the photoinitiator. Preferably, the initiator system is present in a total amount of at least 0.01 wt-%, more preferably, at least 0.03 wt-%, and most preferably, at least 0.05 wt-%, based on the weight of the dental composition. Preferably, the initiator system is present in a total amount of no more than 10 wt-%, more preferably, no more than 5 wt-%, and most preferably, no more than 2.5 wt-%, based on the weight of the dental composition.

Redox Initiator Systems

In certain embodiments, the dental compositions of the present invention are chemically hardenable, i.e., the dental compositions contain a chemically hardenable component and a chemical initiator (i.e., initiator system) that can polymerize, cure, or otherwise harden the dental composition without dependence on irradiation with actinic radiation. Such chemically hardenable dental compositions are sometimes referred to as "self-cure" compositions and may include glass ionomer cements, resin-modified glass ionomer cements, redox cure systems, and combinations thereof.

The chemically hardenable dental compositions may include redox cure systems that include a hardenable component (e.g., an ethylenically unsaturated polymerizable component) and redox agents that include an oxidizing agent and a reducing agent. Suitable hardenable components, redox agents, optional acid-functional components, and optional fillers that are useful in the present invention are described in U.S. Pat. No. 7,173,074 (Mitra et al.) and U.S. Pat. No. 6,982,288 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system to permit ready dissolution in (and discourage separation from) the other components of the hardenable dental composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfonic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. No. 6,982,288 (Mitra et al.).

The reducing and oxidizing agents are present in amounts sufficient to permit an adequate free-radical reaction rate. This can be evaluated by combining all of the ingredients of the hardenable dental composition except for the optional filler, and observing whether or not a hardened mass is obtained.

Preferably, the reducing agent is present in an amount of at least 0.01% by weight, and more preferably at least 0.1% by weight, based on the total weight (including water) of the components of the hardenable dental composition. Preferably, the reducing agent is present in an amount of no greater than 10% by weight, and more preferably no greater than 5% by weight, based on the total weight (including water) of the components of the hardenable dental composition.

Preferably, the oxidizing agent is present in an amount of at least 0.01% by weight, and more preferably at least 0.10% by weight, based on the total weight (including water) of the components of the hardenable dental composition. Preferably, the oxidizing agent is present in an amount of no greater than 10% by weight, and more preferably no greater than 5% by weight, based on the total weight (including water) of the components of the hardenable dental composition.

The reducing or oxidizing agents can be microencapsulated as described in U.S. Pat. No. 5,154,762 (Mitra et al.). This will generally enhance shelf stability of the hardenable dental composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a hardenable dental composition such as described U.S. Pat. No. 5,154,762 (Mitra et al.).

Fillers

In certain preferred embodiments, the hardenable dental composition is unfilled. In other certain embodiments, the hardenable dental composition further includes a filler. Fillers can be selected from one or more of a wide variety of materials suitable for incorporation in compositions used for dental applications, such as fillers currently used in dental restorative compositions, and the like.

The filler is preferably finely divided. The filler can have a unimodal or polymodal (e.g., bimodal) particle size distribution. Preferably, the maximum particle size (the largest dimension of a particle, typically, the diameter) of the filler is less than 30 micrometers, more preferably less than 20 micrometers, and most preferably less than 10 micrometers. Preferably, the average particle size of the filler is less than 0.1 micrometers, and more preferably less than 0.075 micrometer.

The filler can be an inorganic material. It can also be a crosslinked organic material that is insoluble in the resin system (i.e., the hardenable components), and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz (i.e., silica, $SiO_2$); nitrides (e.g., silicon nitride); glasses and fillers derived from, for example, Zr, Sr, Ce, Sb, Sn, Ba, Zn, and Al; feldspar; borosilicate glass; kaolin; talc; zirconia; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like. Further examples of fillers include soft fillers as described, for example, in U.S. Provisional Application Ser. No. 61/101,339 (Amos et al.), filed Sep. 29, 2008.

Preferred non-acid-reactive filler particles are quartz (i.e., silica), submicron silica, zirconia, submicron zirconia, and non-vitreous microparticles of the type described in U.S. Pat. No. 4,503,169 (Randklev). Mixtures of these non-acid-reactive fillers are also contemplated, as well as combination fillers made from organic and inorganic materials.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable dental composition. The glass also typically contains sufficient elutable fluoride ions so that the hardened dental composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like. Silane-treated zirconia-silica ($ZrO_2$—$SiO_2$) filler, silane-treated silica filler, silane-treated zirconia filler, and combinations thereof are especially preferred in certain embodiments.

Other suitable fillers are disclosed in U.S. Pat. No. 6,387,981 (Zhang et al.) and U.S. Pat. No. 6,572,693 (Wu et al.) as well as International Pat. Application Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.); U.S. Pat. No. 7,090,722 (Budd et al.); and U.S. Pat. No. 7,156,911 (Kangas et al.); and U.S. Published Application No. 2005/0256223 A1 (Kolb et al.).

For embodiments in which the hardenable dental composition includes one or more fillers, the hardenable dental composition preferably includes at least 1% by weight filler, more preferably at least 2% by weight filler, and most preferably at least 5% by weight filler. For embodiments in which the hardenable dental composition includes one or more fillers, the hardenable dental composition preferably includes at most 85% by weight filler, more preferably at most 50% by weight filler, and most preferably at most 25% by weight filler.

In certain preferred embodiments, unfilled or lightly filled hardenable dental compositions provide for easy cleanup of excess hardenable and/or hardened dental composition. Lightly filled hardenable dental compositions include at most 35% by weight filler, more preferably at most 20% by weight filler, and most preferably at most 10% by weight filler. Examples of unfilled and/or lightly filled hardenable dental compositions include primers and/or self-etching primers.

In certain preferred embodiments, the hardenable dental composition (e.g., filled or unfilled) is flowable during application, for example, at oral temperatures (e.g., 37° C.) in the methods described herein. As used herein, a "flowable" hardenable dental composition means that the dental composition deforms or flows under its own weight at oral temperatures (e.g., 37° C.). Certain "flowable" hardenable dental compositions deform or flow under their own weight at room temperature (e.g., 20-25° C.).

Optional Photobleachable and/or Thermochromic Dyes

In some embodiments, hardenable dental compositions of the present invention preferably have an initial color remarkably different than dental structures. Color is preferably imparted to the dental composition through the use of a photobleachable or thermochromic dye. The dental composition preferably includes at least 0.001% by weight photobleachable or thermochromic dye, and more preferably at least 0.002% by weight photobleachable or thermochromic dye, based on the total weight of the dental composition. The dental composition preferably includes at most 1% by weight photobleachable or thermochromic dye, and more preferably at most 0.1% by weight photobleachable or thermochromic dye, based on the total weight of the dental composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the dental composition and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and U.S. Pat. No. 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the inventive compositions is initiated by light. Preferably, the dental composition's color change is initiated using actinic radiation using, for example, a dental curing light which emits visible or near infrared (IR) light for a sufficient amount of time. The mechanism that initiates the color change in the dental compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a color test. Using a color test, a value of $\Delta E^*$ is determined, which indicates the total color change in a 3-dimensional color space. The human eye can detect a color change of approximately 3 $\Delta E^*$ units in normal lighting conditions. The dental compositions of the present invention are preferably capable of having a color change, $\Delta E^*$, of at least 20; more preferably, $\Delta E^*$ is at least 30; most preferably $\Delta E^*$ is at least 40.

Miscellaneous Optional Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the dental compositions of the invention can contain additives such as indicators, dyes, pigments, inhibitors, accelerators, viscosity modifiers, wetting agents, buffering agents, stabilizers, and other similar ingredients that will be apparent to those skilled in the art. Viscosity modifiers include the thermally responsive viscosity modifiers (such as PLURONIC F-127 and F-108 available from BASF Wyandotte Corporation, Parsippany, N.J.) and may optionally include a polymerizable moiety on the modifier or a polymerizable component different than the modifier. Such thermally responsive viscosity modifiers are described in U.S. Pat. No. 6,669,927 (Trom et al.) and U.S. Pat. Application Publication No. 2004/0151691 (Oxman et al.).

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Methods

Dental articles (e.g., orthodontic appliances) having a compressible material attached to the surface thereof may be bonded to a tooth structure using methods (e.g., direct or indirect bonding methods) that are well known in the art.

Figure 5:
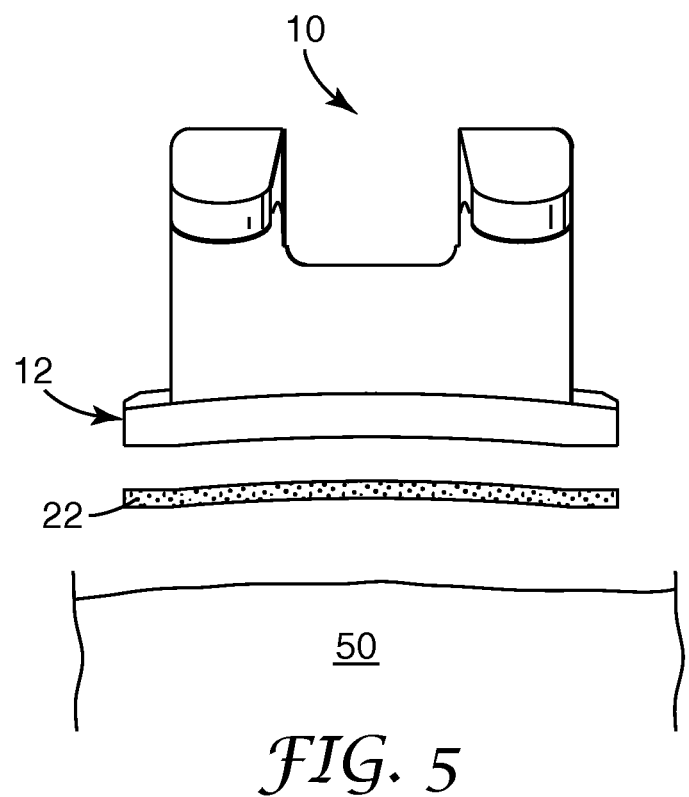
FIG. 5 is an exemplary embodiment of a method of bonding an orthodontic appliance to a tooth structure as described herein, which illustrates an orthodontic appliance, a compressible material, and a tooth structure prior to bonding the orthodontic appliance to the tooth structure.

For the embodiment illustrated in FIG. 5, a hardenable dental composition is in contact with compressible material 22. Compressible material 22 is illustrated in FIG. 5 as not being provided attached to base 12 of orthodontic appliance 10. However, orthodontic appliance 10 can optionally be provided as an assembly having compressible material 22 attached to base 12 of appliance 10 as described herein. For embodiments that encompass indirect bonding methods, base 12 of appliance 10 can be a custom base, which can optionally be formed from a compressed, compressible material as described herein.

In one embodiment, compressible material 22 (either alone or attached to base 12 of orthodontic appliance 10) is supplied having a hardenable dental composition therein. In another embodiment, a hardenable dental composition can be added to compressible material 22 (either alone or attached to base 12 of orthodontic appliance 10) by a practitioner. For example, the practitioner can apply a hardenable dental composition to compressible material 22, or compressible material 22 can be dipped or immersed in a hardenable dental composition.

Figure 6:
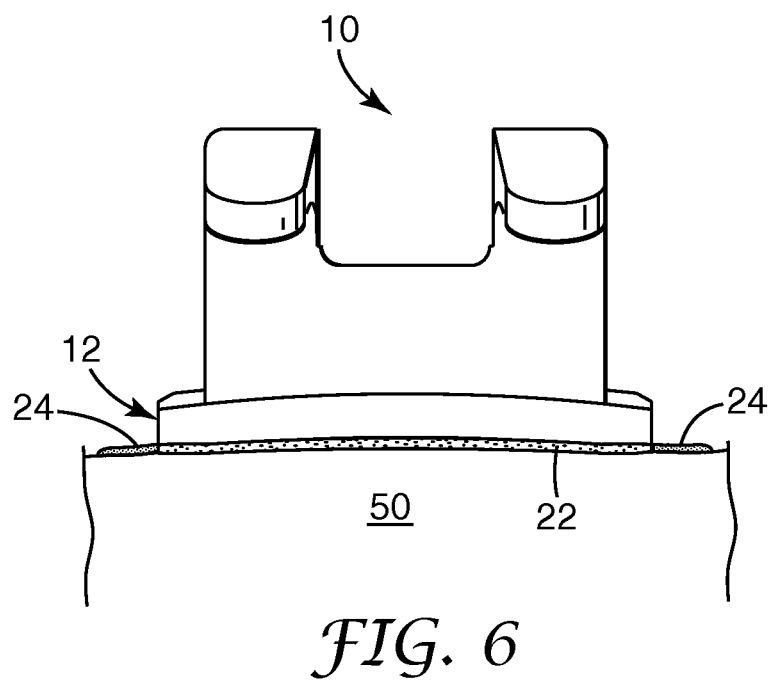
FIG. 6 is an exemplary embodiment of a method of bonding an orthodontic appliance to a tooth structure as described herein, which illustrates an orthodontic appliance, a compressible material, and a tooth structure during or subsequent to bonding the orthodontic appliance to the tooth structure.

A dental article (e.g., an orthodontic appliance) can be bonded to a tooth structure using compressible materials and hardenable dental compositions as described herein, using direct and/or indirect methods. For the embodiment illustrated in FIG. 5, compressible material 22 and a hardenable dental composition is contacted with tooth structure 50 and base 12 of orthodontic appliance 10; and the hardenable dental composition is hardened. During this procedure, the orthodontic appliance is applied to the tooth structure with sufficient pressure to substantially fill any gaps between the appliance and tooth structure as illustrated in FIG. 6. Because the contour of the tooth structure surface may not precisely match the contour of the outer surface of the base 12, compressible material 22 can be essentially completely compressed (e.g., at most 10% original pore volume remaining) in some areas, and essentially uncompressed (e.g., at least 90% of original pore volume remaining), or somewhat compressed in other areas. In certain embodiments, compressing compressible material 22 as completely as possible to minimize the distance between appliance 10 and tooth structure 50 can be advantageous for accurately expressing the prescription of the appliance. For certain embodiments, compressible material 22 can have an initial (uncompressed) thickness of 0.8 millimeters (mm) (0.03 inch) to 2.5 mm (0.1 inch), and a compressed thickness in at least some portions of 0.12 mm (0.005 inch) to 0.25 mm (0.01 inch) (e.g., a compressed thickness that is 0.1 times the uncompressed thickness). As illustrated in FIG. 6, compressing compressible material 22 can cause excess hardenable dental composition 24 to exude from compressed compressible material 22 onto tooth structure 50 at or near the periphery of appliance 10.

In some embodiments, pressure can be applied to the compressible material during hardening to prevent rebound of the compressible material. In other embodiments, the compressible material will remain compressed even after pressure is relieved.

The tooth structure can be untreated or treated. In some embodiments tooth structure 50 is treated with a self-etching primer prior to contacting compressible material 22 with tooth structure 50. For such embodiments, the hardenable dental composition can typically be hardened during or immediately after compressing the compressible material. In some embodiments, the hardenable dental composition is self-etching, and the tooth structure can be untreated prior to applying appliance 10. For such embodiments, the hardenable dental composition preferably contacts the tooth structure for a period of time (e.g., 15 seconds or more) prior to hardening the hardenable dental composition.

Upon application of orthodontic appliance 10 to tooth structure 50, the hardenable dental composition and/or compressible material (e.g., for embodiments in which the compressible material is, for example, a foamed and optionally partially hardened dental composition) can be hardened to adhere the orthodontic appliance to the tooth structure. A variety of suitable methods of hardening the dental composition are known in the art. For example, in some embodiments the hardenable dental composition can be hardened by exposure to UV or visible light. In other embodiments, the hardenable dental composition can be provided as a multi-part composition that hardens upon combining the two or more parts.

The compressible materials as described herein can be used for indirect bonding methods. For indirect bonding methods, orthodontic appliances can be placed, for example, on a model (e.g., replica plaster or "stone" model) of the patient's dental arch to provide a custom base for later mounting on the patient's tooth structure, commonly using a placement device. In one embodiment, the orthodontic appliances have a compressible material attached to the bases thereof for bonding to the replica plaster or "stone" model. Thus, the compressible material can be compressed to form a custom base, for example, upon hardening of a hardenable dental composition. Exemplary indirect bonding methods are described, for example, in U.S. Pat. No. 7,137,812 (Cleary et al.). In another embodiment, brackets are held in place on the model during formation of the placement device using a temporary adhesive. The compressible material and hardenable composition can be added to the bracket base at any time between removal from the model and insertion in the patient's mouth.

In another embodiment, an indirect bonding placement device can be formed about a rapid prototyping model (e.g., prepared by stereolithography, selective laser sintering, fused deposition modeling, and the like, or combinations thereof) of the patient's teeth with appliances attached. Such a rapid prototyping model can be produced from data supplied by a scan of an impression of the patient's teeth, a model of the patient's teeth, or of the teeth directly. Brackets can be held in place during formation of the placement device, for example, by a temporary adhesive or by friction fit with the guides as described, for example, in Published U.S. Pat. Application No. 2006/0257821 (Cinader et al.). Compressible material can be added to the bracket bases following removal from the stereolithography model. For embodiments in which the brackets are held in place by friction fit with the placement guides, compressible material can be attached to the brackets prior to placement in the guides. If not already present, a hardenable dental composition can be added to the compressible material at any time from immediately following removal from the rapid prototyping model to immediately prior to placement in the patient's mouth.

In yet another embodiment of indirect bonding methods, the orthodontic appliance provided in the placement device can include a compressible material attached to a custom base such as a custom lingual appliance (which can optionally be formed from a compressed, compressible material) for bonding to a patient's tooth. Referring to FIG. 7, the placement device 100 (comprising shell 60, matrix material 70, and assemblies 80) is shown in cross-sectional view. The assemblies 80 include appliances having custom bases 82 having compressible material 84 attached thereto. Assemblies 80 can optionally include a hardenable dental composition, which can optionally be in contact with compressible material 84. The placement device 100 can then be placed in a package by the manufacturer and shipped to the practitioner's office.

Once the patient has returned to the office, the bonding procedure is undertaken. After any tooth preparation steps are completed, the package (if present) is opened and placement device 100 is removed from the package. A hardenable dental composition can be added to compressible material 84, for example, if assembly 80 does not already include a hardenable dental composition in contact with compressible material 84. The shell 60 is then positioned over the corresponding teeth and seated, optionally with a swinging, hinge-type motion. In FIG. 7, the patient's tooth is designated by the numeral 90. Since the shape of the cavity of the matrix material 70 matches the shape of the underlying teeth, the assemblies 80 are simultaneously seated against the underlying teeth 90 at precisely the same locations corresponding to the previous position of the assemblies 80 on the replica. Preferably, pressure is then applied to the occlusal, labial and buccal surfaces of the shell 60 until such time as the compressible material 84 has been sufficiently compressed, and oftentimes until the hardenable dental composition and/or compressible material (e.g., for embodiments in which the compressible material is, for example, a foamed and optionally partially hardened dental composition) have been hardened. Optionally, finger pressure may be used to firmly press the assemblies 80 against the enamel surfaces of the patient's teeth 90.

Upon application of assemblies 80 to the enamel surfaces of the patient's teeth 90, the hardenable dental composition and/or compressible material (e.g., for embodiments in which the compressible material is, for example, a foamed and optionally partially hardened dental composition) can be hardened to adhere assemblies 80 to the enamel surfaces of the patient's teeth 90. A variety of suitable methods of hardening the dental composition are known in the art. For example, in some embodiments the hardenable dental composition can be hardened by exposure to UV or visible light. In other embodiments, the hardenable dental composition can be provided as a multi-part composition that hardens upon combining the two or more parts. This multi-part composition can take a form in which the two parts are mixed prior to adding to the compressible material or a form in which one part is applied to the compressible material and one part is applied to the teeth.

Once the hardenable dental composition has hardened, the shell 60 is carefully removed from the patient's dental arch. Preferably, the shell 60 is first separated from the matrix material 70, which remains in place over the dental arch along with the assemblies 80. Next, the matrix material 70 is detached from the assemblies 80. Optionally, a hand instrument such as a scaler may be used to help hold each assembly 80 against the surface of the respective tooth 90 of the patient as the matrix material 70 is peeled away from the assemblies 80. However, in instances where a relatively soft matrix material is employed or otherwise readily releases from the assemblies 80, the use of a scaler to help avoid fracturing the fresh adhesive bond is optional. As another option, the shell 60 may be separated from the matrix material 70 before the hardenable dental composition has hardened. This option is particularly useful when the hardenable dental composition includes a light-curable adhesive. Once the matrix material 70 has been detached from the assemblies 80, an archwire is placed in the slots of the assemblies 80 (e.g., appliances) and ligated in place.

The present invention is also advantageous when used with other types of indirect bonding placement devices. Examples of other indirect bonding placement devices are described in published U.S. Patent Application Nos. 2008/0233528 (Kim et al.), 2008/0233530 (Cinader), 2007/0287120 (Cinader et al.), 2006/0257821 (Cinader, Jr. et al.), and 2006/0223031 (Cinader, Jr. et al.), and U.S. Pat. No. 7,452,205 (Cinader, Jr. et al.).

Advantageously, for embodiments in which the hardenable dental composition is unfilled or lightly filled, the practitioner may not need to remove excess dental composition (e.g., hardened or unhardened) from the tooth structure.

If removal of excess dental composition is desired, removal of unfilled or lightly filled dental composition (e.g., hardened or unhardened) can typically be effected by rinsing with water, applying toothpaste, brushing, or a combination thereof, by the practitioner or patient, which can reduce the risk of dislodging the appliance and/or damaging enamel that can be encountered during removal of excess highly filled hardened dental composition. In another embodiment, such excess unfilled or lightly filled hardenable or hardened dental composition can remain on the tooth as, for example, a sealant that can preferably provide additional protection to the tooth structure.

Objects and advantages of this invention are further illustrated by the following examples. Note however that the particular materials and amounts thereof recited in these examples, as well as other conditions and details, should not be construed to unduly limit this invention. Unless specified otherwise, all parts and percentages are by weight, all water is de-ionized water, all molecular weights are weight average molecular weight, and all chemicals and reagents were obtained from Sigma-Aldrich Corp., located in St. Louis, Mo.

EXAMPLES

As used herein:

"ESPE Sil" refers to a ceramic priming solution (e.g., a silane in ethanol) available under the trade designation ESPE Sil from 3M, St. Paul, Minn.

"Rocatec Plus" refers to silica modified surface roughening media available under the trade designation Rocatec Plus from 3M, St. Paul, Minn.

"TBSLV" refers to an orthodontic adhesive available under the trade designation TRANSBOND Supreme LV from 3M, St. Paul, Minn.

"RelyX Unicem" refers to a self-adhesive resin cement available under the trade designation RelyX Unicem from 3M, St. Paul, Minn.

"Acidic Resin A" refers to an orthodontic primer containing dimethacrylate compounds with acid functionality (e.g., CDMA, the reaction product between citric acid and 2-isocyanatoethyl methacrylate as described, for example, in U.S. Pat. No. 6,960,079 (Brennan et al.)) in combination with other methacrylates (e.g., including polyethyleneglycol dimethacrylate (PEGDMA) and urethane dimethacrylate (UDMA)) similar to those described in Example 2 of U.S. Patent Application Publication No. 2009/0011388 (Craig et al.).

"SEP" refers to an orthodontic self-etching primer available under the trade designation TRANSBOND Plus Self Etching Primer from 3M, St. Paul, Minn.

"TBXT Primer" refers to an unfilled orthodontic primer, available under the trade designation TRANSBOND XT Primer from 3M, St. Paul, Minn.

"TBXT Adhesive" refers to a filled orthodontic adhesive, available under the trade designation TRANSBOND XT Adhesive from 3M, St. Paul, Minn.

Bond Strength Testing

The adhesive strength of brackets bonded to juvenile bovine teeth was determined using the following standardized method. First, each sample was mounted with the gingival tie wings oriented upward in a test fixture attached to a QTEST/5 mechanical testing machine (MTS Systems Corporation, Eden Prairie, Minn.). A 0.020 inch diameter standard round wire was looped under the occlusal tie wings and attached to the crosshead of the testing machine. After initial crosshead position was adjusted to make the wire snug, it was translated upward at 5 millimeters per minute (0.2 inches per minute) until the bracket was debonded. Maximum force was recorded and divided by the measured surface area of the bracket base to obtain bond strength. Each reported bond strength value represents an average of at least ten replicated measurements.

Example 1

To prepare substrates for bond strength testing, juvenile bovine incisors free of soft tissue were embedded in circular acrylic disks with labial surfaces exposed. The labial surfaces of the embedded teeth were then scrubbed with slurry of pumice in water and rinsed. Each tooth was first etched and primed to prepare the enamel surface for bonding. This was accomplished by rubbing SEP for 3-5 seconds onto the enamel surface using the enclosed applicator according to product instructions. A gentle air stream was then directed to the bonding area using an air syringe for approximately 3 seconds to thin out the SEP coating and remove excess moisture.

To prepare the foam for bonding, a 3M Disposable Mini-Sponge Applicator (Product No. 7522S, available from 3M, St. Paul, Minn.), was dipped into the TBXT Primer to fully saturate the foam. The primer-filled foam was then interposed between a Victory Series upper central bracket (Product No. 017-401 or similar, 3M Unitek, Monrovia, Calif.) and the enamel surface. After fully seating the bracket and foam onto the tooth, the primer was cured by irradiating the mesial and distal sides of the bracket for 5 seconds each using an Ortholux LED curing light (3M Unitek, St. Paul, Minn.).

Bonded samples were stored in water at 25° C. for 24 hours. Subsequently, bond strength testing on these samples proceeded according to the procedure described earlier. The results of these tests on Example 1 are given in Table 1.

TABLE 1

Bond strength data on example 1.

| | Mean bond strength (MPa) | Standard deviation (MPa) |
|---|---|---|
| Example 1 | 9.38 | 2.57 |
| Comparative example 1 | 15.6 | 2.57 |

Comparative Example 1

To prepare substrates for bond strength testing, bovine incisors free of soft tissue were embedded in circular acrylic disks with labial surfaces exposed. The labial surfaces of the embedded teeth were then scrubbed with slurry of pumice in water and rinsed. Each tooth was first etched and primed to prepare the enamel surface for bonding. This was accomplished by rubbing SEP for 3-5 seconds onto the enamel surface using a micro-brush applicator according to product instructions. A gentle air stream was then directed to the bonding area using an air syringe to thin out the SEP coating and remove excess moisture.

Approximately 10 milligrams of TBXT Adhesive was then applied via syringe to the base of Victory Series upper central brackets (just enough to cover the bracket base). The bracket with adhesive was fully seated onto the tooth surface and the excess adhesive removed from the periphery of the bracket base. The adhesive was then cured by irradiating the mesial and distal sides of the bracket for 5 seconds each using an Ortholux LED curing light.

All bonded samples were stored in water at 25° C. for 24 hours. Subsequently, bond strength testing on these samples proceeded according to the procedure described earlier. The bond strength results on comparative example 1 are also shown in Table 1. The comparison between the foam based adhesive and control adhesive show that the foam adhesive produced significantly lower bond strength. However, both adhesives yield clinically acceptable bond strengths exceeding 8 MPa per bracket. Standard deviation in measured bond strength was similar between the two adhesives.

Example 2

To prepare substrates for bond strength testing, juvenile bovine incisors free of soft tissue were embedded in circular acrylic disks with labial surfaces exposed. The labial surfaces of the embedded teeth were then scrubbed with slurry of pumice in water, rinsed, and dried. Each tooth was then etched and primed to prepare the enamel surface for bonding. This was accomplished by rubbing SEP for 3-5 seconds onto the enamel surface using the enclosed applicator according to product instructions. A gentle stream of oil-free compressed air was then directed to the bonding area for approximately 3 seconds to thin out the SEP coating.

To prepare a bracket for bonding, a Victory Series bracket (Product No. 017-401, -402, -501, or -502 from 3M Unitek, Monrovia, Calif.) was sandblasted with Rocatec Plus for approximately 3 seconds at 2.8 bar (0.28 megapascals). ESPE Sil was then applied to the bonding base and allowed to dry at room temperature for five minutes.

A bonding base-shaped punch was used to cut out pieces of a glass fiber filter available under the trade designation Pall Type A/C Glass Fiber Filter from Pall Corporation, East Hills, N.Y. ESPE Sil was applied to the glass fibers and allowed to dry at room temperature for five minutes.

TBSLV was then applied to the bonding base of a bracket prepared as described above, then skimmed off such that the wire mesh was just filled. A base-shaped piece of the ESPE Sil treated glass fibers was then pressed onto the bonding base using light finger pressure, the pressure was released, and the TBSLV was at least partially hardened by irradiating the bracket for 5 seconds from the bonding base side using an Ortholux LED curing light (3M Unitek, St. Paul, Minn.). TBXT primer was then applied to the glass fibers with a microbrush.

The bracket was then pressed onto the tooth using finger pressure, the pressure was released, and the adhesive was then cured by irradiating the mesial and distal sides of the bracket for 5 seconds each using an Ortholux LED curing light to give the bonded sample.

Example 3

Bonded samples were prepared in a manner similar to that described in Example 2, except that a glass fiber filter available under the trade designation Pall TCLP Glass Fiber Filter from Pall Corporation, East Hills, N.Y. was used instead of Pall Type A/C Glass Fiber Filter.

Comparative Example 2

Substrates for bond strength testing were prepared in a manner similar to that described in Example 2.

A Victory Series bracket (Product No. 017-401, -402, -501, or -502 from 3M Unitek, Monrovia, Calif.) having TBXT adhesive on the bonding base was pressed onto the tooth using finger pressure. The flash was cleaned, the pressure was released, and the adhesive was then cured by irradiating the mesial and distal sides of the bracket for 5 seconds each using an Ortholux LED curing light to give the bonded sample.

Bonded samples were stored in water at 37° C. for 16 to 24 hours. Subsequently, bond strength testing on these samples proceeded according to the procedure described earlier. The results of these tests on Examples 2 and 3, and Comparative Example 2 are shown in Table 2.

TABLE 2

Bond strength data on Examples 2 and 3, and Comparative Example 2.

| | Mean bond strength (MPa) | Standard deviation (MPa) |
|---|---|---|
| Example 2 | 20.7 | 4.5 |
| Example 3 | 19.9 | 3.5 |
| Comparative Example 2 | 18.9 | 6.5 |

Example 4

Substrates for bond strength testing and brackets for bonding were prepared in a manner similar to that described in Example 2.

A bonding base-shaped punch was used to cut out pieces of Whatman 934AH glass fiber filter available from Whatman Inc., Piscataway, N.J. ESPE Sil was applied to the glass fibers and allowed to dry at room temperature for five minutes.

RelyX Unicem was then applied to the bonding base of a bracket prepared as described above, then skimmed off such that the wire mesh was just filled. A base-shaped piece of the ESPE Sil treated glass fibers was then pressed onto the bonding base using finger pressure, the pressure was released, and the RelyX Unicem was at least partially hardened by irradiating the bracket for 5 seconds from the bonding base side using an Ortholux LED curing light. TBXT primer was then applied to the glass fibers with a microbrush.

The bracket was then pressed onto the tooth using finger pressure, the pressure was released, and the adhesive was then cured by irradiating the mesial and distal sides of the bracket for 5 seconds each using an Ortholux LED curing light to give the bonded sample.

Comparative Example 3

Substrates for bond strength testing were prepared in a manner similar to that described in Example 2.

A Victory Series bracket (Product No. 017-401, -402, -501, or -502 from 3M Unitek, Monrovia, Calif.) having TBXT adhesive on the bonding base was pressed onto the tooth using finger pressure. The flash was cleaned, the pressure was released, and the adhesive was then cured by irradiating the mesial and distal sides of the bracket for 5 seconds each using an Ortholux LED curing light to give the bonded sample.

Bonded samples were stored in water at 37° C. for 16 to 24 hours. Subsequently, bond strength testing on these samples proceeded according to the procedure described earlier. The results of these tests on Example 4 and Comparative Example 3 are shown in Table 3.

TABLE 3

Bond strength data on Example 4 and Comparative Example 3.

|  | Mean bond strength (MPa) | Standard deviation (MPa) |
| --- | --- | --- |
| Example 4 | 21.6 | 4.4 |
| Comparative Example 3 | 19.2 | 6.8 |

Example 5

Substrates for bond strength testing and brackets for bonding were prepared in a manner similar to that described in Example 2.

A bonding base-shaped punch was used to cut out pieces of Whatman 934AH glass fiber filter available from Whatman Inc., Piscataway, N.J. ESPE Sil was applied to the glass fibers and allowed to dry at room temperature for five minutes.

TBSLV was then applied to the bonding base of a bracket prepared as described above, then skimmed off such that the wire mesh was just filled. A base-shaped piece of the ESPE Sil treated glass fibers was then pressed onto the bonding base using finger pressure, the pressure was released, and the TBSLV was at least partially hardened by irradiating the bracket from the bonding base side for 5 seconds using an Ortholux LED curing light. Acidic Resin A was then applied to the glass fibers with a microbrush.

A thin coat of saliva was applied to the tooth surface using a microbrush applicator. The bracket was then pressed onto the tooth using finger pressure, the pressure was released, and the adhesive was then cured by irradiating the mesial and distal sides of the bracket for 5 seconds each using an Ortholux LED curing light to give the bonded sample.

Example 6

Bonded samples were prepared in a manner similar to that described in Example 5, except that TBXT primer was applied to the glass fibers instead of Acidic Resin A.

Comparative Example 4

Substrates for bond strength testing were prepared in a manner similar to that described in Example 2.

A thin coat of saliva was applied to the tooth surface using a microbrush applicator. A Victory Series bracket (Product No. 017-401, -402, -501, or -502 from 3M Unitek, Monrovia, Calif.) having TBXT adhesive on the bonding base was pressed onto the tooth using finger pressure. The flash was cleaned, the pressure was released, and the adhesive was then cured by irradiating the mesial and distal sides of the bracket for 5 seconds each using an Ortholux LED curing light to give the bonded sample.

Bonded samples were stored in water at 37° C. for 16 to 24 hours. Subsequently, bond strength testing on these samples proceeded according to the procedure described earlier. The results of these tests on Examples 5 and 6, and Comparative Example 4 are shown in Table 4.

TABLE 4

Bond strength data on Examples 5 and 6, and Comparative Example 4.

|  | Mean bond strength (MPa) | Standard deviation (MPa) |
| --- | --- | --- |
| Example 5 | 15.6 | 5.6 |
| Example 6 | 14.0 | 5.4 |
| Comparative Example 4 | 17.3 | 7.7 |

Example 7

Substrates for bond strength testing were prepared in a manner similar to that described in Example 2. Victory Series brackets (Product No. 017-401, -402, -501, or -502 from 3M Unitek, Monrovia, Calif.) were used without further preparation.

A bonding base-shaped punch was used to cut out pieces of Whatman 934AH glass fiber filter available from Whatman Inc., Piscataway, N.J. ESPE Sil was applied to the glass fibers and allowed to dry at room temperature for five minutes.

TBXT adhesive was then applied to the bonding base of a bracket prepared as described above, then skimmed off such that the wire mesh was just filled. A base-shaped piece of the ESPE Sil treated glass fibers was then pressed onto the bonding base using finger pressure, the pressure was released, and the TBXT adhesive was at least partially hardened by irradiating the bracket from the bonding base side for 5 seconds using an Ortholux LED curing light. TBXT primer was then applied to the glass fibers with a microbrush.

The bracket was then pressed onto the tooth using finger pressure, the pressure was released, and the adhesive was then cured by irradiating the mesial and distal sides of the bracket for 5 seconds each using an Ortholux LED curing light to give the bonded sample.

Example 8

Substrates for bond strength testing were prepared in a manner similar to that described in Example 2. Victory Series brackets (Product No. 017-401, -402, -501, or -502 from 3M Unitek, Monrovia, Calif.) were used without further preparation.

A bonding base-shaped punch was used to cut out pieces of a Whatman 934AH glass fiber filter available from Whatman Inc., Piscataway, N.J. ESPE Sil was applied to the glass fibers and allowed to dry at room temperature for five minutes.

TBXT adhesive was then applied to the bonding base of a bracket prepared as described above, then skimmed off such that the wire mesh was just filled. A base-shaped piece of the ESPE Sil treated glass fibers was then pressed onto the bonding base using finger pressure. TBXT primer was then applied to the glass fibers with a microbrush.

The bracket was then pressed onto the tooth using finger pressure, the pressure was released, and the adhesive was then cured by irradiating the mesial and distal sides of the bracket for 5 seconds each using an Ortholux LED curing light to give the bonded sample.

Example 9

Bonded samples were prepared in a manner similar to that described in Example 8, except that the brackets for bonding were prepared in a manner similar to that described in Example 2.

Comparative Example 5

Substrates for bond strength testing were prepared in a manner similar to that described in Example 2.

A Victory Series bracket (Product No. 017-401, -402, -501, or -502 from 3M Unitek, Monrovia, Calif.) having TBXT adhesive on the bonding base was pressed onto the tooth using finger pressure. The flash was cleaned, the pressure was released, and the adhesive was then cured by irradiating the mesial and distal sides of the bracket for 5 seconds each using an Ortholux LED curing light to give the bonded sample.

Bonded samples were stored in water at 37° C. for 16 to 24 hours. Subsequently, bond strength testing on these samples proceeded according to the procedure described earlier. The results of these tests on Examples 7, 8, and 9, and Comparative Example 5 are shown in Table 5.

TABLE 5

Bond strength data on Examples 7, 8, and 9, and Comparative Example 5.

|  | Mean bond strength (MPa) | Standard deviation (MPa) |
|---|---|---|
| Example 7 | 15.4 | 3.3 |
| Example 8 | 15.1 | 4.1 |
| Example 9 | 17.7 | 4.8 |
| Comparative Example 5 | 19.9 | 5.1 |

Example 10

To prepare substrates for bond strength testing, 6.35 mm (0.25 inch) diameter burundum rods were embedded in circular acrylic disks with the cylindrical surfaces exposed. ESPE Sil was then applied to the exposed surfaces of the burundum rods and the samples were placed in an oven at 100° C. for 1 hour. Each rod was then primed to prepare the surface for bonding. This was accomplished by applying TBXT Primer to the rod. A gentle stream of oil-free compressed air was then directed to the bonding area for approximately 3 seconds to thin out the primer coating.

Brackets for bonding were prepared in a manner similar to that described in Example 2.

A bonding base-shaped punch was used to cut out pieces of a nonwoven available under the trade designation Novenette 149-051 from Ahlstrom Corporation (Bishopville, S.C.).

TBSLV was then applied to the bonding base of a bracket prepared as described above, then skimmed off such that the wire mesh was just filled. A base-shaped piece of the nonwoven was then pressed onto the bonding base using finger pressure, the pressure was released, and the TBSLV was at least partially hardened by irradiating the bracket from the bonding base side for 5 seconds using an Ortholux LED curing light. TBXT primer was then applied to the nonwoven with a microbrush.

The bracket was then pressed onto the rod using finger pressure, the pressure was released, and the adhesive was then cured by irradiating the mesial and distal sides of the bracket for 5 seconds each using an Ortholux LED curing light to give the bonded sample.

Example 11

Bonded samples were prepared in a manner similar to that described in Example 10, except that a nonwoven available under the trade designation HEF 140-114 (Spunlaced) from Ahlstrom Corporation (Bishopville, S.C.) was used instead of BBA Novenette 149-051 nonwoven.

Example 12

Bonded samples were prepared in a manner similar to that described in Example 10, except that a nonwoven available under the trade designation 70GSM Nylon Spunbond from Cerex Advanced Fabrics, Inc. (Cantonment, Fla.) was used instead of BBA Novenette 149-051 nonwoven.

Example 13

Bonded samples were prepared in a manner similar to that described in Example 10, except that a nonwoven available under the trade designation Sontara 8005 from Dupont (Wilmington, Del.) was used instead of BBA Novenette 149-051 nonwoven.

Comparative Example 6

Substrates for bond strength testing were prepared in a manner similar to that described in Example 10.

A Victory Series bracket (Product No. 017-401, -402, -501, or -502 from 3M Unitek, Monrovia, Calif.) having TBXT adhesive on the bonding base was pressed onto the rod using finger pressure. The flash was cleaned, the pressure was released, and the adhesive was then cured by irradiating the mesial and distal sides of the bracket for 5 seconds each using an Ortholux LED curing light to give the bonded sample.

Bonded samples were stored in water at 37° C. for 16 to 24 hours. Subsequently, bond strength testing on these samples proceeded according to the procedure described earlier. The results of these tests on Examples 10, 11, 12, and 13, and Comparative Example 6 are shown in Table 6.

TABLE 6

Bond strength data on Examples 10, 11, 12, and 13, and Comparative Example 6.

|  | Mean bond strength (MPa) | Standard deviation (MPa) |
|---|---|---|
| Example 10 | 9.5 | 6.2 |
| Example 11 | 18.1 | 5.4 |
| Example 12 | 13.4 | 4.1 |
| Example 13 | 18.2 | 5.8 |
| Comparative Example 6 | 19.8 | 5.6 |

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An assembly comprising:
   a dental article for bonding to tooth structure, the article having an outer surface;
   a compressible material attached to the surface of the article, wherein the compressible material is capable of being reduced in volume on application of pressure used to place the article on the tooth structure and is a porous material selected from the group consisting of foams, sponges, nonwoven fabrics, nonwoven mats, glass wool, cotton fibers, cellulose fibers, and combinations thereof; and
   a hardenable dental composition at least partially within the compressible material that, during use, is configured to form a bond with tooth structure, wherein the compressible material forms at least part of the bond.

2. The assembly of claim 1 wherein at least a portion of the outer surface of the article is selected from the group consisting of a machined base, a molded base, a mesh base, and combinations thereof.

3. The assembly of claim 1 wherein at least a portion of the outer surface of the article comprises glass grit.

4. The assembly of claim 1 wherein the compressible material is mechanically bonded to the surface of the article, chemically bonded to the surface of the article, or a combination thereof.

5. The assembly of claim 1 wherein the compressible material is attached to the surface of the article by one of an unhardened dental composition, a partially hardened dental composition, and a hardened dental composition.

6. The assembly of claim 1 wherein the dental article is an orthodontic appliance.

7. The assembly of claim 1 wherein the porous material comprises pores in communication.

8. The assembly of claim 1 wherein the compressibility of the compressible material is at least 0.9 and no greater than 0.001.

9. The assembly of claim 1 wherein the foams are selected from the group consisting of cellulose foams, glass foams, ceramic foams, polymeric foams, a foamed dental composition, and combinations thereof.

10. The assembly of claim 9 wherein the foamed dental composition is at least partially hardened hardenable dental composition.

11. The assembly of claim 1, wherein the hardenable dental composition forms a continuous layer on the surface of the compressible material opposite the outer surface of the dental article.

12. The assembly of claim 1 wherein the hardenable dental composition comprises no greater than 25% filler, based on the total weight of the composition.

13. The assembly of claim 1 wherein the hardenable dental composition comprises:
   an ethylenically unsaturated compound; and
   a hardener.

14. The assembly of claim 1 wherein the hardenable dental composition is flowable.

15. The assembly of claim 14 wherein the flowable, hardenable dental composition is unfilled or lightly filled.

16. The assembly of claim 14 wherein the hardenable dental composition comprises at most 10% by weight filler, based on the total weight of the hardenable dental composition.

17. The assembly of claim 1 wherein the hardenable dental composition is a primer or a self-etching primer.

18. The assembly of claim 1 wherein the compressible material has an external surface having a concave configuration when relaxed.

19. The assembly of claim 1 wherein the compressible material has a generally uniform thickness.

20. The assembly of claim 1 wherein the area of the compressible material is smaller than the area of the outer surface of the article to which it is attached.

21. A kit comprising two or more assemblies according to claim 1.

22. The kit of claim 21 comprising at least two assemblies having different mats or scrims for use on different teeth.

23. The kit of claim 21 wherein the assemblies comprise one or more orthodontic appliances.

24. The kit of claim 21 further comprising a self-etching primer.

25. The assembly of claim 1, wherein the compressible material is opaque.

26. The assembly of claim 1, wherein the porous material comprises a plurality of fibers, and wherein the fibers are tied together to form a mat or scrim.

27. The assembly of claim 1, wherein the hardenable dental composition comprises one part of a two-part hardenable dental composition.

28. The assembly of claim 1, wherein the hardenable dental composition comprises one part of a two-part redox pair.

29. The assembly of claim 1, wherein the hardenable dental composition is patterned on a surface of the compressible material.

30. The assembly of claim 1, further comprising one or more additional layers of dental composition in contact with the compressible material.

31. The assembly of claim 30, wherein the one or more additional layers of dental composition comprises at least one patterned layer.

32. The assembly of claim 1, wherein the hardenable dental composition has an initial color prior to exposure to actinic radiation and a final color subsequent to exposure to actinic radiation, said initial color being different than said final color.

33. The assembly of claim 1, wherein the hardenable composition is at least partially within the porous, compressible material.

34. The assembly of claim 1, wherein, during use, application of pressure to the compressible material causes hardenable dental composition to exude from compressed compressible material onto tooth structure at or near a periphery of the article surface.

35. A method for bonding a dental article to a tooth structure, the method comprising:
providing a dental article having an outer surface;
providing a compressible material and a hardenable dental composition;
contacting the compressible material and the hardenable dental composition with the tooth structure and the surface of the dental article, wherein the compressible material is capable of being reduced in volume on application of pressure used to place the article on the tooth structure and is a porous material selected from the group consisting of foams, sponges, nonwoven fabrics, nonwoven mats, glass wool, cotton fibers, cellulose fibers, and combinations thereof; and
hardening the dental composition to create a bond between the dental composition and the tooth structure, the compressible material forming part of the bond.

36. The method of claim 35 wherein the compressible material is attached to the outer surface, and wherein the act of contacting includes the act of compressing the compressible material between the tooth structure and the outer surface.

37. The method of claim 35 wherein the dental article is an orthodontic appliance.

38. The method of claim 37 wherein the tooth structure comprises a tooth model, and hardening the dental composition forms a custom base on the orthodontic appliance for use in an indirect bonding method.

39. The method of claim 37 wherein at least a portion of the tooth structure is selected from the group consisting of a natural tooth surface, an artificial tooth surface, and combinations thereof.

40. The method of claim 39 wherein the artificial tooth surface is in the form of a crown, a bridge, a partial denture, or a pontic.

41. The method of claim 35 wherein providing a compressible material and a hardenable dental composition comprises contacting a porous, compressible material with a hardenable dental composition.

42. The method of claim 35 wherein the hardenable dental composition is a primer or a self-etching primer.

43. The method of claim 35 wherein contacting the compressible material and the hardenable dental composition with the tooth structure and the surface of the dental article and hardening the dental composition comprise bonding the dental article to the tooth structure, and wherein bonding the dental article to the tooth structure does not comprise removing excess hardenable or hardened dental composition.

44. The method of claim 35 further comprising removing excess hardenable or hardened dental composition.

45. The method of claim 44 wherein removing excess hardenable or hardened dental composition comprises rinsing with water, applying toothpaste, brushing, or a combination thereof.

46. The method of claim 35, wherein bonding the dental article to the tooth structure does not require at least one of etching or priming the tooth structure.

47. The assembly of claim 1, wherein the compressibility of the compressible material is at least 0.7 and no greater than 0.01.

48. The method of claim 35, wherein the compressibility is at least 0.7 and no greater than 0.01.

49. The method of claim 35, wherein the compressible material forms at least part of the bond.

50. An assembly comprising:
a dental article for bonding to tooth structure, the article having an outer surface; and
a porous, compressible material attached to the surface of the article, wherein, during use, the compressible material is reduced in volume on application of pressure used to place the article on the tooth structure and, upon application of said pressure, filling a gap between the surface and the tooth structure, and wherein at least a portion of the compressible material exhibits a reduction in volume of at least 30% and no greater than 99% on the application of pressure used to place the article on the tooth structure; and
a flowable, hardenable dental composition in contact with the compressible material and operable to form a bond with tooth structure, wherein the flowable, hardenable dental composition is a composition comprising no greater than 25% filler.

51. The assembly of claim 50, wherein the flowable, hardenable dental composition is a composition comprising no greater than 20% filler.

52. The assembly of claim 50, wherein the hardenable dental composition comprises a hardenable component and a hardener.

53. The assembly of claim 50, wherein the compressible material is an inelastic material.

54. The assembly of claim 50, wherein the compressible material is selected from the group consisting of sponges, nonwoven fabrics, glass wool, cotton fibers, cellulose fibers, glass fibers, and combinations thereof.

55. The assembly of claim 50, wherein, during use, application of pressure to the compressible material causes hardenable dental composition to exude from compressed compressible material onto tooth structure.

56. The assembly of claim 50, wherein the compressible material is, during use, compressed between the tooth and the outer surface.

* * * * *